United States Patent
Ward et al.

(10) Patent No.: US 6,673,346 B1
(45) Date of Patent: Jan. 6, 2004

(54) COMPOSITIONS AND METHODS FOR THE TREATMENT OF SEPSIS

(75) Inventors: Peter A. Ward, Ann Arbor, MI (US); Markus Huber-Lang, South Lyon, MI (US); Vidya Sarma, Ann Arbor, MI (US); Boris Czermak, Frieburg (DE)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/387,671

(22) Filed: Aug. 31, 1999

(51) Int. Cl.$^7$ ...................... A61K 39/395; C07K 16/44
(52) U.S. Cl. .................. 424/158.1; 424/130.1; 424/139.1; 424/172.1; 530/389.2; 530/389.3
(58) Field of Search ................. 530/387.9, 388.1, 530/388.15, 388.25, 326, 328, 329, 389.2, 389.3; 424/130.1, 139.1, 141.1, 145.1, 158.1, 172.1

(56) References Cited

U.S. PATENT DOCUMENTS

| | | | |
|---|---|---|---|
| 4,357,272 A | | 11/1982 | Polson |
| 5,051,448 A | | 9/1991 | Shashoua |
| 5,169,862 A | | 12/1992 | Burke, Jr. et al. |
| 5,192,746 A | | 3/1993 | Lobl et al. |
| 5,260,203 A | | 11/1993 | Ladner et al. |
| 5,340,923 A | * | 8/1994 | Carroll |
| 5,539,085 A | | 7/1996 | Bischoff et al. |
| 5,559,103 A | | 9/1996 | Gaeta et al. |
| 5,565,332 A | | 10/1996 | Hoogenboom et al. |
| 5,576,423 A | | 11/1996 | Aversa et al. |
| 5,585,089 A | | 12/1996 | Queen et al. |
| 5,658,727 A | | 8/1997 | Barbas et al. |
| 5,904,922 A | | 5/1999 | Carroll |

FOREIGN PATENT DOCUMENTS

| | | |
|---|---|---|
| EP | 025949 | 4/1981 |
| EP | 0 245 993 | 11/1987 |
| WO | WO 96/39503 | 12/1996 |

OTHER PUBLICATIONS

Zhong et al. PNAS 94:13856–13861, Dec. 1997.*
Hatherill et al. Journal od Biological Response Modifiers, 8(6):614–24, Dec. 1989.*
Czermak et al., Nature Medicine 5(7):788–792, Jul. 1999.*
Larrick et al. Infect. Immunity 55:1867–72, 1987.*
NCBI Accession No. A57689, Feb. 1997.*
NCBI Accession No. P12082, Feb. 1996.*
NCBI Accession No. P01032, Feb. 1996.*
The Pierce Catalog (1994) pp. T–52 and T–289.*
Janeway et al (Immunobiology 1997) London, pp. 378–380.*
Ames et al., "Isolation of Neutralizing Anti–C5a Monoclonal Antibodies from a Filamentous Phage Monovalent Fab Display Library," *J. of Immunology* 152:4572–4581 (1994).
Bone, "The Pathogenesis of Sepsis," *Ann. Intern. Med.* 115:457–469 (1991).
Caplan, et al., "Infection Surveillance and Control in the Severely Traumatized Patient," *Am. J. Med.* 70:638–640 (1981).
Caruthers et al., "New chemical methods for synthesizing polynucleotides," *Nuc. Acids Res. Symp. Ser.* 7:215–233 (1980).
Chow and Kempe, "Synthesis of oligodeoxyribonucleotides on silica gel support," *Nuc. Acids Res.* 9:2807–2817 (1981).
Crea and Horn, "Synthesis of oligonucleotides on cellulose by a phosphotriester methods," *Nuc. Acids Res.* 9:2331 (1980).
Creighton (1983) *Proteins Structures And Molecular Principles*, W H Freeman and Co, New York N.Y., Title page.
Czemak et al., "Protective effects of C5a blockade in sepsis," *Nature* 5:788–792 (1999).
Davis et al., *Basis Methods in Molecular Biology*, (1986), Title page.
Elzaim, et al., "Generation of Neutralizing Antipeptide Antibodies to the Enzymatic Domain of *Pseudomonas aeruginosa* Exotoxin A," *Infect. Immun.* May;66(5):2170–9 (1998).
Evans et al., "An engineered poliovirus chimaera elicits broadly reactive HIV–1 neutralizing antibodies," *Nature* 339:385 (1989).
Gerard, C. et al., "Amino Acid Sequence of the Anaphylatoxin from the Fifth Component of Porcine Complement," *J. Biol. Chem.* 255(10), 4710–4715, (1980).
Gluzman, "SV40–Transformed Simian Cell Support the Replication of Early SV40 Mutants," *Cell* 23:175 [1981].
Hill, J.H. and Ward, P.A., "The Phlogistic Role of C3 Leukotactic Fragments in Myocardial Infarcts of RatsI," *J. Exp. Med.* 133:885–900, (1971).
Hochuli et al., "New Metal Chelate Adsorbent Selective For Proteins And Peptides Containing Neighbouring Histidine Residues," *J. Chromatography* 411:177 (1987).
Hoffman et al., "Prognostic Variables for Survival of Neonatal Foals Under Intensive Care," *J. Vet. Int. Med.* 6:89–95 (1992).
Huang et al., "Vaccinia Virus Recombinants Expressing an 11–Kilodalton β–Galactosidase Fusion Protein Incorporate Active β–Galactosidase in Virus Particles," *J. Virol.* 62:3855 (1988).
Joklik et al. (eds.), "*Streptococcus pneumoniae*," *Zinsser Microbiology*, 18th ed., p. 485, Appleton–Century–Crofts, Norwalk, CT (1984).

(List continued on next page.)

*Primary Examiner*—Christina Chan
*Assistant Examiner*—F. Pierre VanderVegt
(74) *Attorney, Agent, or Firm*—Hedlen & Carroll, LLP

(57) ABSTRACT

The present invention relates to compositions and methods for the prevention and treatment of blood-borne and toxin mediated diseases, and in particular anti-C5a antibodies for the prevention and treatment of sepsis in humans as well as other animals. The present invention also relates to methods of generating anti-C5a antibodies employing C-terminal truncated C5a peptides.

3 Claims, 11 Drawing Sheets

OTHER PUBLICATIONS

Kennet, R.H., "*Monoclonal Antibodies, Hybridoma—A New Dimension in Biological Analysis,*" Plenum Press, NY (1980).

Kettleborough, et al., "Humanization of a mouse monoclonal antibody by CDR–grafting: the importance of framework residues on loop conformation," *Protein Engineering*, vol. 4, No. 7, pp 773–783 (1991).

Kohl, J., Bitter–Suermann, D., *Anaphylatoxins. Complement in health and disease.*, Edited by Whaley, K., Loos, M., Weiler, J.M., Kluwer Academic publishers, pp 299–324, (1993).

Kohler, G. and Milstein, C., "Continuous cultures of fused cells secreting antibody of predefined specificity," *Nature* 256:495 (1975).

Kola et al., "Epitope mapping of a C5a neutralizing mAb using a combined approach of phage display, synthetic peptides an site=directed mutagenesis," *Immunotechnology* 1:115–126 (1996).

Kozbor and Roder, "The production of monoclonal antibodies fromhuman lymphocytes," *Immunol. Today* 4:72–79 (1983).

Machiedo et al., "Patterns Of Mortality In a Surgical Inventive Care Unit," *Surg. Gyn. & Obstet.* 152:757–759 (1981).

Mandecki W, et al., "Chemical Synthesis of a gene encoding the human complement fragment C5a and its expression of *Escherichia coli,*" *Proc Natl Acad Sci U S A.* Jun.82(11):3543–7(1985).

Matteucci and Caruthers, "The Synthesis of Oligodeoxypyrimidines on a Polymer Support," *Tetrahedron Lett* 21:719 (1980).

Meek et al., "The Baltimore Sepsis Scale: Measurement of Sepsis in Patients with Burns Using a New Scoring System," *J. Burn Care Rehab.* 12:564–568 (1991).

Mohr et al., "Effects of anti–C5a monoclonal antibodies on oxygen use in a porcine model of severe sepsis," *European Journal of Clinical Investigation* 28:227–234 (1998).

Morris et al., "Endotoxemia in neonatal calves given antiserum to a mutant *Escherichia coli* (J–5)," *Am. J. Vet. Res.* 47:2554–2565 (1986).

Mulligan, M.S. et al., "Requirement and Role of C5a in Acute Lung Inflammatory Injury in Rats," *J. Clin. Invest.* 98:503–512, 1996).

Nardelli et al., "A Chemically Defined Synthetic Vaccine Model for HIV–1[1]," *J. Immunol.* 148:914 (1992).

Nichols, "Classification of Surgical Wounds and Nonoperative Factors Influencing Surgical Wound Infection," *Decision Making in Surgical Sepsis*, B.C. Decker, Inc., Philadelphia, pp. 20–21 (1991).

Nilsson et al., "Affinity Fusion Strategies for Detection, Purification, and Immobilization of Recombinant Proteins," *Prot. Expr. Purif.*, 11(1):1–16 [1997].

Olson et al., "The Role of C5 in Septic Lung Injury," *Ann. Surg.* 202:771–776 (1985).

Park et al., "Attenuation of Endothelium–Dependent Dilation of Pig Pulmonary Arterioles After Cardiopulmonary Bypass is Prevented by Monoclonal Antibody to Complement C5a," *Anesth Anag* 89:42–9 (1999).

Posnett et al., "A Novel Method for Producing Anti–peptide Antibodies," *JBC* 263:1719 (1988).

Roberge et al., "A Strategy for a Convergent Synthesis of N–Linked Glycopeptides on a Solid Support," *Science* 269:202–204 (1995).

Rothermel et al., "Nucleotide and corrected amino acid sequence of the functional recombinant rat anaphylatoxin C5a[1]," *Biochim. Biophys. Acta* 1351 (1–2), 9–12, (1997).

Schlienger et al., "Human Immunodeficiency Virus Type 1 Major Neutralizing Determinant Exposed on Hepatitis B Surface Antigen Particles Is Highly Immunogenic in Primates," *J. Virol.* 66:2 (1992).

Schulman et al., "Cost–effectiveness of HA–1A Monoclonal Antibody for Gram–Negative Sepsis," *JAMA* 266:3466–3471 (1991).

Slack and I.S. Snyder, *Bacteria and Human Disease*, pp. 128–133, Yearbook Medical Publishers (1978).

Solomkin, J.S., et al., "Neutrophil dysfunction in sepsis. II. Evidence for the role of complement activation products in cellular deactivation," *Surgery* 90:319–327 (1981).

Stahel, et al., "TNF–α–Mediated Expression of the Receptor for Anaphylatoxin C5a on Neurons in Experimental *Listeria meningoencephalitis,*" *J. Immunol.* Jul. 15;159(2):861–9 (1997).

Stevens et al., "Effects of Anti–C5a Antibodies on the Audult Respiratory Distress Syndrome in Septic Primates," *J. Clin. Invest.* 77:1812–1816 (1986).

Stryer et al., *Biochemistry*, 2nd ed,, WH Freeman and C.[1981], Title page.

Van Epps, et al., "Relationship of C5a Receptor Modulation to the Functional Responsiveness of Human Polymorphonuclear Leukocytes of C5a[1]," *J. Immunol.* 150:246–252 (1993).

Ward, P.A. & Becker, E.L., "The Deactivation of Rabbit Neutrophils by Chemotactic Factor and the Nature of the Activatable Esterase," *J. Exp. Med.* 127:693–709 (1968).

Wilson et al., "The Structure of an Antigenic Determinant in a Protein," *Cell* 37:767–778 (1984).

Wolff, "Monoclonal Antibodies And The Treatment Of Gram–Negative Bacteremia And Shock," *New Eng. J. Med.* 324:486–488 (1991).

Youmans et al., *Biologic and Clinical Basis of Infections Diseases*, 3d ed., p. 553, W.B. Saunders Co., (1985).

Zarbock, J., et al., "A proton nuclear magnetic resonance study of the conformation of bovine anaphylatoxin C5a in solution," *FEBS Lett.* 238(2), 289–294, (1988).

\* cited by examiner

SEQUENCES SELECTED FOR HUMAN C5a

```
         |              |              |
         10             20             30
         |              |              |
————————————————————————————————————————————
1  MLQKKIEEIAAKYKHSVVKKCCYDGA*VNNDE
                     — — — —  = = = = = = = =
————————————————————————————————————————————

|              |              |
         40             50             60
         |              |              |
————————————————————————————————————————————
33 TCEQRAARISLGPRCIKAFTECCVVASQLRAN
   = = = = = =

… # COMPOSITIONS AND METHODS FOR THE TREATMENT OF SEPSIS

This invention was made with Government support under the National Institutes of Health (NIH) awarded by contract GM29507 and HL31963. The government has certain rights in this invention.

FIELD OF THE INVENTION

The present invention relates to compositions and methods for the prevention and treatment of blood-borne and toxin-mediated diseases, and in particular anti-C5a antibodies for the prevention and treatment of sepsis in humans as well as other animals.

BACKGROUND OF THE INVENTION

Sepsis is a major cause of morbidity and mortality in humans and other animals. It is estimated that 400,000–500,000 episodes of sepsis resulted in 100,000–175,000 human deaths in the U.S. alone in 1991. Sepsis has become the leading cause of death in intensive care units among patients with non-traumatic illnesses. [G. W. Machiedo et al., *Surg. Gyn. & Obstet.* 152:757–759 (1981).] It is also the leading cause of death in young livestock, affecting 7.5–29% of neonatal calves [D. D. Morris et al., *Am. J. Vet. Res.* 47:2554–2565 (1986)], and is a common medical problem in neonatal foals. [A. M. Hoffinan et al., *J. Vet. Int. Med.* 6:89–95 (1992).] Despite the major advances of the past several decades in the treatment of serious infections, the incidence and mortality due to sepsis continues to rise. [S. M. Wolff, *New Eng. J. Med.* 324:486–488 (1991).]

Sepsis is a systemic reaction characterized by arterial hypotension, metabolic acidosis, decreased systemic vascular resistance, tachypnea and organ dysfunction. Sepsis can result from septicemia (i.e., organisms, their metabolic end-products or toxins in the blood stream), including bacteremia (i.e., bacteria in the blood), as well as toxemia (i.e., toxins in the blood), including endotoxemia (i.e., endotoxin in the blood). The term "bacteremia" includes occult bacteremia observed in young febrile children with no apparent foci of infection. The term "sepsis" also encompasses fungemia (i.e., fungi in the blood), viremia (i.e., viruses or virus particles in the blood), and parasitemia (i.e., helminthic or protozoan parasites in the blood). Thus, septicemia and septic shock (acute circulatory failure resulting from septicemia often associated with multiple organ failure and a high mortality rate) may be caused by a number of organisms.

The systemic invasion of microorganisms presents two distinct problems. First, the growth of the microorganisms can directly damage tissues, organs, and vascular function. Second, toxic components of the microorganisms can lead to rapid systemic inflammatory responses that can quickly damage vital organs and lead to circulatory collapse (i.e., septic shock) and oftentimes, death.

There are three major types of sepsis characterized by the type of infecting organism. Gram-negative sepsis is the most common and has a case fatality rate of about 35%. The majority of these infections are caused by *Escherichia coli, Klebsiella pneumoniae* and *Pseudomonas aeruginosa*. Gram-positive pathogens such as the Staphylococci and Streptococci are the second major cause of sepsis. The third major group includes fungi, with fungal infections causing a relatively small percentage of sepsis cases, but with a high mortality rate.

Many of these infections are acquired in a hospital setting and can result from certain types of surgery (e.g., abdominal procedures), immune suppression due to cancer or transplantation therapy, immune deficiency diseases, and exposure through intravenous catheters. Sepsis is also commonly caused by trauma, difficult newborn deliveries, and intestinal torsion (especially in dogs and horses).

Many patients with septicemia or suspected septicemia exhibit a rapid decline over a 24–48 hour period. Thus, rapid methods of diagnosis and treatment delivery are essential for effective patient care. Unfortunately, a confirmed diagnosis as to the type of infection traditionally requires microbiological analysis involving inoculation of blood cultures, incubation for 18–24 hours, plating the causative organism on solid media, another incubation period, and final identification 1–2 days later. Therefore, therapy must be initiated without any knowledge of the type and species of the pathogen, and with no means of knowing the extent of the infection.

It is widely believed that anti-endotoxin antibody treatment administered after sepsis is established may yield little benefit because these antibodies cannot reverse the inflammatory cascade initiated by endotoxin. In addition, the high cost of each antibody could limit physicians' use of a product where no clear benefit has been demonstrated. [K. A. Schulman et al., *JAMA* 266:3466–3471 (1991).] Furthermore, these endotoxin antibodies only target gram-negative sepsis, and no equivalent antibodies exist for the array of gram-positive organisms and fungi.

Clearly, there is a great need for agents capable of preventing and treating sepsis. It would be desirable if such agents could be administered in a cost-effective fashion. Furthermore, approaches are needed to combat all forms of sepsis.

SUMMARY OF THE INVENTION

The present invention relates to compositions and methods for the prevention and treatment of blood-borne and toxin mediated diseases, and in particular anti-C5a antibodies for the prevention and treatment of sepsis in humans as well as other animals.

The present invention provides a composition comprising antibody specific for complement component C5a peptide. In another embodiment, the composition comprises antibody which is specific for complement component C5a peptide, wherein the C5a peptide has a C-terminal region and an N-terminal region, and the antibody is not reactive with the C-terminal region. In further embodiments, the antibody is specific for the N-terminal region of complement component C5a peptide. In an additional embodiment, the antibody is also not reactive with complement component C5 protein.

It is not intended that the present invention be limited to antibodies specific for C5a peptides from certain animals. In certain embodiments, the antibody is specific for rat C5a peptide. In other embodiments, the antibody is specific for bovine C5a peptide. In still other embodiments, the antibody is specific for porcine C5a peptide. In a preferred embodiment, the antibody is specific for human C5a peptide.

It is also not intended that the present invention be limited to antibodies generated in a particular animal. A variety of animals are useful for generating the antibodies of the present invention. In one embodiment, the antibody is generated in an animal selected from a mouse, a rat, a horse, a goat, a chicken, and a rabbit. In some embodiments, the antibodies are collected from the blood of the animal. In other embodiments, the animal generating the antibodies is a bird, and the antibodies are collected from egg yolk.

It is not intended that the present invention be limited to the nature of the antibodies, as a variety of antibody types are contemplated. In one embodiment, the antibodies are monoclonal. In another embodiment, the antibodies are humanized. In other embodiments, the antibodies are chimaeric. In a preferred embodiment, the antibodies are polyclonal.

The present invention also provides a method of producing polyclonal antibody. In one embodiment, the method comprises, providing; an animal and an immunogenic composition, wherein the composition comprises C-terminal truncated C5a peptides; and immunizing the animal with the immunogenic composition in order to generate antibodies. In some embodiments, the immunogenic composition comprises adjuvant. In a further embodiment, antibodies are collected from the animal.

It is not intended that the present invention be limited to antibodies specific for C5 a peptides from any particular animal. In certain embodiments, the antibody is specific for rat C5a peptide. In other embodiments, the antibody is specific for bovine C5a peptide. In still other embodiments, the antibody is specific for porcine C5a peptide. In a preferred embodiment, the antibody is specific for human C5a peptide.

It is not intended that the present invention be limited to particular C-terminal truncated peptides. A variety of C-terminal truncated peptides are contemplated. In one embodiment, the C-terminal truncated peptide corresponds to the entire N-terminal region of C5a peptide. In another embodiment, the C-terminal truncated peptide corresponds to the entire N-terminal region of C5a peptide and a portion of the C-terminal region. In another embodiment, the C-terminal truncated peptide is a fragment or portion of the N-terminal region of C5a peptide. In another embodiment, the C-terminal truncated C5a peptide is between approximately 5 and 50 amino acids in length. In some embodiments, the C-terminal truncated peptide is approximately fifty amino acids in length. In other embodiments, the C-terminal truncated peptide is approximately five amino acids in length. In preferred embodiments, the C-terminal truncated peptides are 20 amino acids in length. In certain embodiments, the C-terminal truncated peptides are selected from SEQ ID NOS:2, 4, 5, 14, 15, and 16.

The present invention also provides a method of treating a subject with the antibodies of the present invention. In one embodiment, the method comprises; providing; a subject, and a therapeutic composition comprising an antibody specific for complement component C5a peptide, wherein the C5a peptide has a C-terminal region and an N-terminal region, and wherein the antibody is not reactive with the C-terminal region; and administering the therapeutic composition to the subject. In another embodiment, the antibody is specific for the N-terminal region of complement component C5a peptide.

In one embodiment, the present invention provides a method comprising; providing; a subject, and a therapeutic composition comprising an antibody specific for complement component C5a peptide, wherein the C5a peptide has a C-terminal region and an N-terminal region, and wherein the antibody is not reactive with the C-terminal region; and administering the therapeutic composition to the subject. In another embodiment, administering the therapeutic composition reduces the binding of complement component C5a peptide to one or more neutrophils of the subject. In a certain embodiment, administering the therapeutic composition reduces bacteremia in the subject. In yet another embodiment, administering the therapeutic composition increases the $H_2O_2$ production of neutrophils of the subject.

In a preferred embodiment, administering the therapeutic composition reduces the symptoms of sepsis.

It is not intended that the therapeutic method of the present invention be limited to particular subjects. A variety of subjects are contemplated. In one embodiment the subject is selected from a pig, a rat, a cow, a horse, and a human. In one embodiment, the therapeutic composition is administered to a subject suffering from symptoms of sepsis. In another embodiment, the therapeutic composition is administered prophylactically to a subject at risk for sepsis, including new born humans and animals.

It is not intended that the therapeutic method of the present invention be limited to certain modes of administration. A variety of modes of administering the therapeutic composition are contemplated. In one embodiment, the therapeutic composition is administered by a mode selected from intravenously, intra-muscularly, subcutaneously, intradermally, intraperitoneally, intrapleurally, intrathecally, and topically.

It is not intended that the present invention be limited to a particular therapeutic composition. A variety of compositions are contemplated. In one embodiment the therapeutic composition comprises a soluble mixture of anti-C5a antibodies. In another embodiment, the anti-C5a antibodies are provided together with physiologically tolerable liquid, gels, solid carriers, diluents, adjuvants or excipients, and combinations thereof. In other embodiments, the therapeutic composition comprises anti-C5a antibodies and other therapeutic agents (e.g. other immunoglobulins or antibiotics).

The present invention also provides a method for screening C-terminal truncated C5a peptides to identify immunogens for the production of anti-C5a antibodies. In one embodiment, the method comprises, providing a C-terminal truncated C5a peptide, modifying the amino acid sequence of said C-terminal truncated C5a peptide, and screening said C-terminal truncated C5a peptide to identify immunogens for the production of anti-C5a antibodies. In one embodiment, the C-terminal truncated C5a peptide which is provided is selected from SEQ ID NO:2, SEQ ID NO:4, SEQ ID NO:5, SEQ ID NO:14, SEQ ID NO: 15, and SEQ ID NO:16. In other embodiments, the screening step involves a chemotaxis assay (See e.g. Examples 7, 8 and 11). In a different embodiment, the screening step involves a competitive binding assay (See e.g. Examples 10 and 11). In an additional embodiment, the screening step involves administering the C-terminal truncated peptides to septic animals (See e.g. Example 11).

DESCRIPTION OF THE FIGURES

FIG. 8 shows the amino acid sequence of human C5a peptide and various smaller portions of the human C5a peptide.

DEFINITIONS

Figure 1:
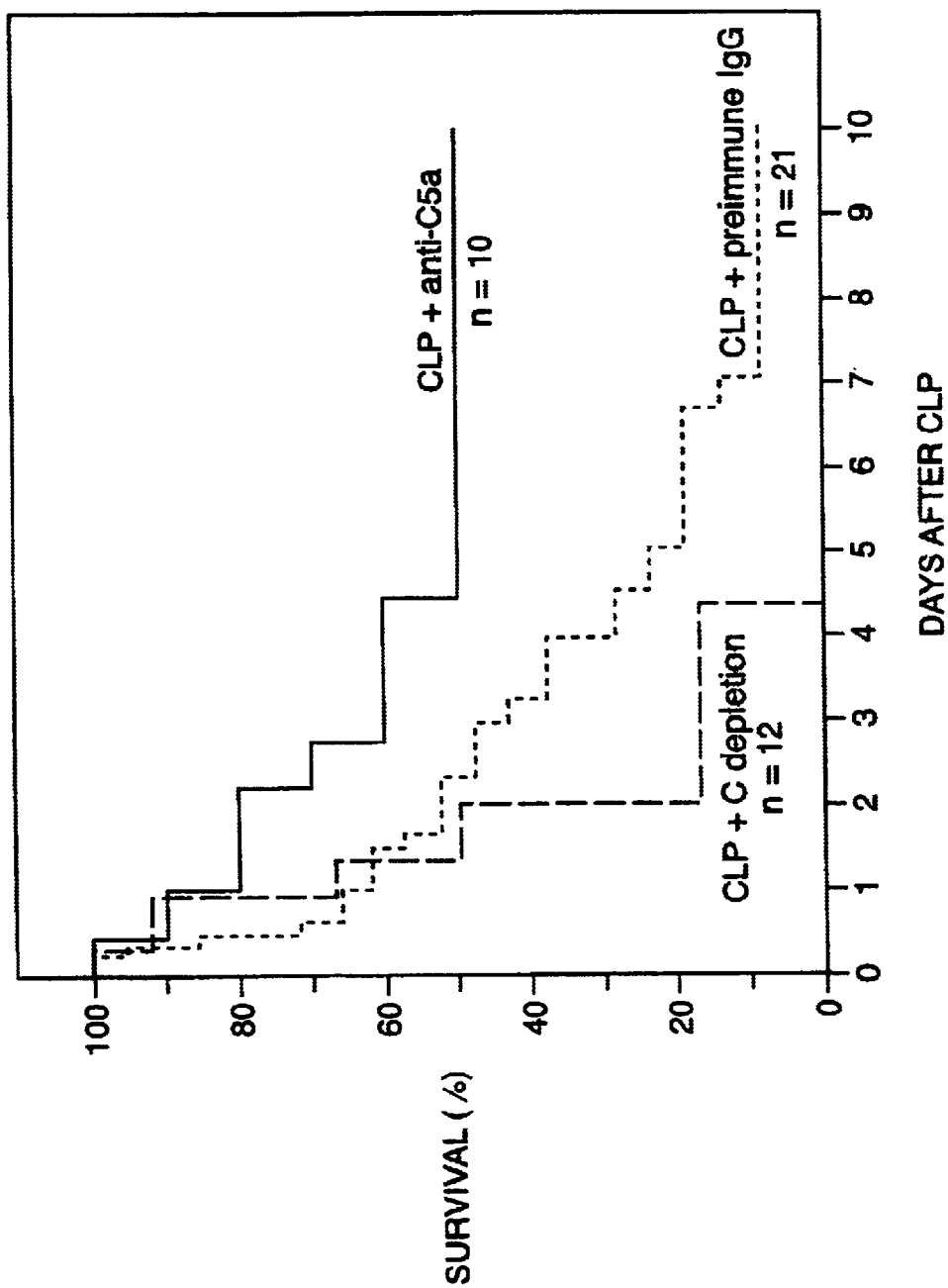
FIG. 1 shows survival curves of septic rats with and without the administration of anti-C5a antibodies.

The phrase "symptoms of sepsis" refers to any symptoms characteristic of a subject with sepsis including but not limited to, arterial hypotension, metabolic acidosis, fever, decreased systemic vascular resistance, tachypnea and organ dysfunction. Sepsis can result from septicemia (i.e., organisms, their metabolic end-products or toxins in the blood stream), including bacteremia (i.e., bacteria in the blood), as well as toxemia (i.e., toxins in the blood), including endotoxemia (i.e., endotoxin in the blood). The term "sepsis" also encompasses fungemia (i.e., fungi in the blood), viremia (i.e., viruses or virus particles in the blood), and parasitemia (i.e., helminthic or protozoan parasites in the blood). Thus, phenotypes associated with septicemia and septic shock (acute circulatory failure resulting from septicemia often associated with multiple organ failure and a high mortality rate) are symptoms of sepsis.

The phrase "reduces the symptoms of sepsis" refers to a qualitative or quantitative reduction in detectable symptoms, including but not limited to a detectable impact on the rate of recovery from disease.

The phrase "at risk for sepsis" in reference to a subject is herein defined as a subject predisposed to the development of sepsis by virtue of the subject's medical status, including but not limited to such factors as infection, trauma (e.g., abdominal perforation, such as by a gun shot wound), surgery (e.g., intestinal surgery), and invasive procedures (e.g., placement of a catheter, etc.) and the like.

As used herein, the term "antigen" refers to any agent (e.g., any substance, compound, molecule [including macromolecules], or other moiety), that is recognized by an antibody, while the term "immunogen" refers to any agent (e.g., any substance, compound, molecule [including macromolecules], or other moiety) that can elicit an immunological response in an individual. These terms may be used to refer to an individual macromolecule or to a homogeneous or heterogeneous population of antigenic macromolecules. It is intended that the term encompasses protein and peptide molecules or at least one portion of a protein or peptide molecule, which contains one or more epitopes. In many cases, antigens are also immunogens, thus the term "antigen" is often used interchangeably with the term "immunogen." The substance may then be used as an antigen in an assay to detect the presence of appropriate antibodies in the serum of the immunized animal.

The term "specific for" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general (i.e. non-specific or background binding).

The term "not reactive with" when used in reference to the potential interaction of an antibody and a protein or peptide means that the antibody does not recognize or bind specifically to that particular protein (i.e. binding is at background levels).

The term "operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression As used herein, the phrase "anti-C5a antibody" refers to antibodies which are specific for complement component C5a peptide, or portions thereof.

As used herein, the term "adjuvant" is defined as a substance known to increase the immune response to other antigens when administered with other antigens. If adjuvant is used, it is not intended that the present invention be limited to any particular type of adjuvant—or that the same adjuvant, once used, be used all the time. It is contemplated that adjuvants may be used either separately or in combination. The present invention contemplates all types of adjuvant, including but not limited to agar beads, aluminum hydroxide or phosphate (alum), Incomplete Freund's Adjuvant, as well as Quil A adjuvant commercially available from Accurate Chemical and Scientific Corporation, Gerbu adjuvant also commercially available (GmDP; C.C. Biotech Corp.), and bacterin (i.e., killed preparations of bacterial cells).

As used herein, the term "N-terminal region of C5a peptide" refers to the N-terminal 50% of the complement component C5a peptide.

As used herein, the term "C-terminal region of C5a peptide" refers to the C-terminal 30% of the complement component C5a peptide.

As used herein, the term "wherein said antibody is not reactive with the C-terminal of C5a region" refers to antibodies that do not recognize or bind to the C-terminal 30% of the C5a peptide.

As used herein, the term "C-terminal truncated C5a peptides" refers to peptides of varying lengths derived from the N-terminal 70% of the C5a peptide, which do not include amino acid sequences from the C-terminal 30% of the C5a peptide. Examples of these peptides include, but are not limited to, SEQ ID NO:2 (from Rat C5a peptide), and SEQ ID NO:4, SEQ ID NO:5, SEQ ID NO:14, SEQ ID NO:15, and SEQ ID NO:16 (from Human C5a peptide).

As used herein, the terms "C5a peptide", "C5a protein", and "complement component C5a peptide" all refer to the complement component peptide in animals which is cleaved from the amino terminus of complement component C5 when the complement system is activated. Examples of animals with this protein include, but are not limited to, mice, rats, cows, pigs, and humans. This definition also includes peptides with synthetic sequences which share substantial homology to naturally occurring C5a peptides. An example of this type of sequence, includes, but is not limited to, the sequence disclosed in Mandecki W, et al., *Proc Natl Acad Sci USA*. June;82(11):3543–7(1985).

As used herein, the term "modifying the amino acid sequence" of said C-terminal truncated C5a peptide refers to the addition, deletion, or substitution of one or more amino acids to create a variant or modified C-terminal truncated C5a peptide (See section II.b, below). Examples of such variants or modified sequences are listed in Table 3 below.

A "variant" of a C5a peptide (or C-terminal truncated C5a peptide) is defined as an amino acid sequence which differs by one or more amino acids from the C5a peptide (or C-terminal truncated C5a peptide) sequence. The variant may have "conservative" changes, wherein a substituted amino acid has similar structural or chemical properties, e.g. replacement of leucine with isoleucine. More rarely, a variant may have "nonconservative" changes, e.g. replacement of glycine with a tryptophan. Similar minor variations may also include amino acid deletions or insertions (i.e., additions), or both. A variant may be an epitope as short as four amino acids in length, and as long as a modified full-lenth C5a peptide. More preferably, a variant is greater than five amino acids in length, and less than twenty-five amino acids in length. Variants may also contain a fusion protein. In such cases, the variant may have more amino acids than the natural, full-lenght C5a peptide.

DESCRIPTION OF THE INVENTION

The present invention relates to compositions and methods for the prevention treatment of blood-borne and toxin mediated diseases, and in particular anti-C5a antibodies for the prevention and treatment of sepsis caused by various types of organisms in humans as well as other animals. It is contemplated that the present invention finds use in the treatment of gram-negative and gram-positive sepsis. Although the invention may be used for treatment of sepsis due to an individual organism, it may also be used to treat sepsis caused by multiple organisms (e.g., sepsis and/or bacteremia due to gram-negative and gram-positive organisms).

I. The C5a Peptide and Sepsis

The complement system is a complex group of proteins present in body fluids that, working together with antibodies or other factors, plays an important role as mediators of immune, allergic, immunochemical and immunopathological reactions. Activation of the complement system can result in a wide range of reactions such as lysis of various kinds of cells, bacteria and protozoa, inactivation of viruses, and the direct mediation of inflammatory processes. Through the hormone-like activity of several of its components, the complement system can recruit and enlist the participation of other humoral and cellular effector systems. These in turn can induce directed migration of leukocytes, trigger histamine release from mast cells, and stimulate the release of lysosomal constituents from phagocytes.

The complement system consists of at least twenty distinct plasma proteins capable of interacting with each other, with antibodies, and with cell membranes. Many of these proteins, when activated, combine with still others to form enzymes that cleave and activate still other proteins in the system. The sequential activation of these proteins follows two main pathways, the classical pathway and the alternative pathway. Both pathways use a common terminal trunk that leads to cell lysis or virus inactivation.

The classical pathway can be activated by antigen-antibody complexes, aggregated immunoglobulins and non-immunological substances such as DNA and trypsin-like enzymes. The classical pathway includes activation of C1, C4, C2 and C3. These components can be grouped into two functional units: C1 or recognition unit; and C4, C2 and C3 or activation unit. Five additional components denominated C5, C6, C7, C8, and C9 define the membrane attack unit forming the terminal trunk common to both pathways.

C5a peptide, also called anaphylatoxin, is a complement component peptide which is cleaved from the amino terminus of component C5 when the complement system is activated. C5a peptide has been shown to stimulate contraction of smooth muscle, enhance vascular permeability, promote the synthesis and release of other mediators including leukotrienes, prostaglandins, platelet-activating factor, and histamine. In vivo, C5a peptide results in the accumulation of polymorphonuclear leukocytes (PMN) (i.e. neutrophils) and marcrophages at the site of inflammation, one of the hallmark events of an acute inflammatory response. In vitro, C5a peptide is a potent chemotaxin for leukocytes, most notably PMN and macrophages, and it activates PMN causing them to release a variety of hydrolytic enzymes and to generate oxygen radicals. These latter phenomena are thought to be responsible not only for the killing of microorganisms but for much of the tissue destruction that takes place in inflammatory situations.

There is abundant evidence that in sepsis, complement activation, production of cytokines, and unregulated inflammatory responses occurs. It is well established in humans with sepsis that complement activation and complement consumption have occurred, as defined by loss of whole hemolytic activity of serum complement (CH50) and the presence of C5a peptide in serum [Koehl, J., Bitter-Suermann, D., *Anaphylatoxins. Complement in health and disease.*, Edited by Whaley, K., Loos, M., Weiler, J. M., Kluwer Academic publishers, pp 299–324, (1993), and Solomkin, et al., *Surgery* 90:319–327, (1981)].

It is well established from in vitro studies that interaction of C5a peptide with C5a receptor (C5aR) leads to phosphorylation of serine residues of the receptor, followed by rapid internalization of the receptor-ligand complex, dephosphorylation of the receptor and its recycling back to the surface of the cell. All of this occurs fairly rapidly. Furthermore, the maximal C5a-induced $H_2O_2$ response of the neutrophil requires that only a fraction of C5aR be occupied with ligand [Van Epps, et al., *J. Immunol.* 150:246–252 (1993)]. Neutrophils stimulated with C5a peptide become refractory ("deactivated") to further stimulation with this peptide; following exposure to high doses of C5a peptide, global deactivation to chemotactic peptides occurs [Ward, P. A. & Becker, E. L., *J. Exp. Med.* 127:693–709 (1968)]. There is clinical evidence that blood neutrophils from humans with early sepsis lose functional responsiveness to C5a peptide and in the latter phases of sepsis lose responsiveness to structurally different chemotaxins such as the bacterial chemotactic factor [Solomkin, J. S., et al., *Surgery* 90:319–327 (1981)]. It has also been reported that C5 deficient mice demonstrate somewhat prolonged survival times when sepsis is induced, but ultimately all animals succumbed to the sepsis syndrome [Olson, L. M., et al., *Ann. Surg.* 202:771–776 (1985)].

It is not necessary to the successful practice the present invention that one understand the precise mechanism by which a therapeutic benefit is achieved, nor is the present invention limited to any particular mechanistic explanation. However, it is believed that sepsis results in excessive production of C5a peptides, which leads to deactivation of neutrophils, compromising the respiratory burst ($H_2O_2$ production) of these cells and the closely linked bactericidal function, which is dependent upon $H_2O_2$ generation and participation of myeloperoxidase. The anti-C5a antibodies of the present invention, therefore, are believed to prevent the deactivation of neutrophils caused by sepsis, thus preserving the bactercidial function of the neutrophils. In this regard, the present invention contemplates antibodies specific for complement component C5a peptides and methods of using these antibodies to treat sepsis. In some embodiments, these antibodies are specific for complement component C5a peptide, wherein said C5a peptide has a C-terminal region and an N-terminal region, and wherein said antibody is not reactive with said C-terminal region.

II. Generating Antibodies to C5a Peptides a. Antibodies

The present invention contemplates monoclonal, polyclonal, and humanized antibodies to C5a peptides. In some embodiments, the antibodies are specific for complement component C5a peptide, wherein said C5a peptide has a C-terminal region and an N-terminal region, and said antibody is not reactive with said C-terminal region.

Monoclonal antibodies useful in this invention are obtained, for example, by well known hybridoma methods. In one embodiment, an animal is immunized with a preparation containing C-terminal truncated peptides. A fused cell hybrid is then formed between antibody-producing cells from the immunized animal and an immortalizing cell such as a myeloma. In one embodiment, antibodies of the present invention are produced by murine hybridomas formed by fusion of mouse myeloma or hybridoma which does not secrete antibody with murine spleen cells which secrete antibodies obtained from mice immunized against C-terminal truncated C5a peptides.

In some embodiments, mice are immunized with a primary injection of C-terminal truncated C5a peptides, followed by a number of boosting injections. During or after the immunization procedure, sera of the mice may be screened to identify mice in which a substantial immune response to the C-terminal truncated C5a peptides has been evoked. From the selected mice, spleen cells are obtained and fusions are performed. Suitable fusion techniques include, but are not limited to, the Sendai virus technique [Kohler, G. and Milstein, C., *Nature* 256:495 (1975)] or the polyethylene glycol method [Kennet, R. H., "*Monoclonal Antibodies, Hybridoma—A New Dimension in Biological Analysis*," Plenum Press, N.Y. (1980)].

The hybridomas are then screened for production of anti-C5a antibodies. Suitable screening techniques include, but are not limited to, solid phase radioimmunoassay. A solid phase immunoadsorbent is prepared by coupling C5a peptides to an insoluble matrix. The immunoadsorbent is brought into contact with culture supernatants of hybridomas. After a period of incubation, the solid phase is separated from the supernatants, then contacted with a labelled antibody against murine immunoglobulin. Label associated with the immunoadsorbent indicates the presence of hybridoma products reactive with C5a peptides.

In preferred embodiments the monoclonal anti-C5a antibodies are produced in large quantities by injecting anti-C5a antibody producing hybridoma cells into the peritoneal cavity of mice and, after an appropriate time, harvesting acites fluid from the mice which yield a high titer of homogenous antibody. The monoclonal antibodies are isolated therefrom. Alternatively, the antibodies are produced by culturing anti-C5a antibody producing cells in vitro and isolating secreted monoclonal anti-C5a antibodies from the cell culture medium directly.

Another method of forming antibody-producing cells is by viral or oncogenic transformation. For example, a B-lymphocyte which produces anti-C5a specific antibody is infected and transformed with a virus, such as the Epstein-Barr virus, to give an immortal antibody-producing cell [Kozbon and Roder, *Immunol. Today* 4:72–79 (1983)].

The present invention also contemplates anti-C5a polyclonal antibodies. Polyclonal antibodies can be prepared by immunizing an animal with a crude preparation of C-terminal truncated C5a peptides, or purified C-terminal truncated C5a peptides. The animal is maintained under conditions whereby antibodies reactive with the components of the peptides are produced. [See e.g. Elzaim, et al., *Infect. Immun.* May;66(5):2170–9 (1998)]. Typically the animal is "boosted" by additional immunizations to increase the antibody titer. In one method, blood is collected from the animal upon reaching a desired titer of antibodies. The serum containing the polyclonal antibodies (antisera) is separated from the other blood components. The polyclonal antibody-containing serum may be further separated into fractions of particular types of antibodies (e.g. IgG or IgM) or mono-specific antibodies can be affinity purified from polyclonal antibody containing serum. In another method, the immunized animal is a bird. In this method antibodies (IgY) are collected from egg yolks. The egg yolk is separated from the yolk lipid and non-antibody proteinaceous matter, recovering the IgY anti-C5a antibodies in purified form (see e.g. U.S. Pat. No. 4,357,272 to Polson and U.S. Pat. No. 5,904,922 to Carroll).

The present invention also contemplates humanized antibodies (i.e. substantially non-immunogenic antibodies). Such antibodies are particularly useful in treating human subjects. Chimeric and 'reshaped' humanized anti-C5a antibodies may be produced according to techniques known in the art (see e.g. U.S. Pat. No. 5,585,089 to Queen et al., and Kettleborough, et al., *Protein Engineering*, vol. 4, no.7, pp 773–783, 1991). In one embodiment, humanized anti-C5a chimeric antiboides are produced using a combinatorial approach (see e.g. U.S. Pat. No. 5,565,332 to Hoogenboom et al. and U.S. Pat. No. 5,658,727 to Barbas et al.). The present invention also contemplates single polypeptide chain binding molecules which have binding specificity and affinity subtantially similar to the binding specificity and affinity of the light and heavy chain aggregate variable region of an anti-C5a antibody (see e.g. U.S. Pat. No. 5,260,203 to Ladner et al.).

b. C5a Peptide Immunogens

The present invention provides various C5a peptide immunogens. For example, the C5a peptides can be from various animals (e.g. human, rat, pig, and cow). The amino acid sequence of these C5a peptides are described in the literature [see Rothermel et al., *Biochim. Biophys. Acta* 1351 (1–2), 9–12, (1997){rat}; Babkina, I. N., et al., *Bioorg Khim*, May;21(5):359–64, (1995){human}; Gerard, C. et al., *J. Biol. Chem.* 255(10), 4710–4715, (1980){pig}; and Zarbock, J., et al., *FEBS Lett.* 238(2), 289–294, (1988) {cow}]. The C5a immunogen may be the full length C5a peptide, or various peptides derived from the full length C5a peptide. In particular embodiments, the peptides are C-terminal truncated peptides (e.g. SEQ ID NOS:2, 4, 5, 14, 15 and 16). Representative sequences are listed in Table 1. Representative human and rat DNA sequences which are used to generate various C-terminal truncated C5a peptides are listed in Table 2, along with the full human and full rat C5a DNA sequences. Modifications of these sequences (i.e. longer/shorter sequence, from various regions) are contemplated by the present invention. Generation of these various C-terminal truncated C5a peptide immunogens are described below.

Variants of the C-terminal truncated C5a peptides are contemplated as useful immunogens (See e.g. Table 3). For example, it is contemplated that an isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (See e.g., Stryer ed., *Biochemistry*, 2nd ed., W H Freeman and Co.[1981]).

Thus, in certain embodiments, modifications of the C-terminal truncated C5a peptides are contemplated by the present invention. Similar minor variations may also include amino acid deletions or insertions (i.e. additions), or both. Guidance in determining which and how many amino acid residues may be substituted, inserted or deleted without abolishing biological or immunological activity may be found using computer programs well known in the art, for example, DNAStar software or GCG (Univ. of Wisconsin).

Whether a change in the amino acid sequence of a C-terminal truncated C5a peptide results in a useful immunogen for producing the anti-C5a antibodies of the present invention can be readily determined. One method involves screening the C-terminal truncated C5a peptides for the ability to inhibit the chemotaxis of neutrophils. Useful immunogens are identified by the ability to induce chemotaxis (See e.g. Examples 7, 8 and 11). Another indication of a useful immunogen is the ability of the C-terminal truncated C5a peptide to inhibit chemotaxis when combined with C5a peptide (See e.g. Examples 7, 8, and 11). Another method involves screening the C-terminal truncated C5a peptides for the ability to antagonize the binding of labelled C5a peptides to neutrophils in a competitive assay (See e.g. Examples 10 and 11). Yet another method involves administering the C-terminal truncated C5a peptides to CLP sepsis induced rats, and monitoring their response over a given time period. Useful immunogens are identified by the ability to reduce the symptoms of sepsis, and/or increase survival times of the rats (See e.g. Example 11).

The C-terminal truncated C5a peptides employed in the present invention may also comprise a fusion partner. Examples of fusion partners include Protein A, ABP, GST, poly histidine, HA, KLH, and MBP. Other fusion partners are well known in the art. (See Nilsson et al., *Prot. Expr. Purif.*, 11(1):1–16 [1997]). The fusion partner may serve various functions, including, but not limited to, enhancement of the solubility of the C-terminal truncated C5a peptides, as well as providing an "affinity tag" to allow the purification of the recombinant fusion C-terminal truncated C5a peptide from the host cell or culture supernatant, or both. If desired, the exogenous protein fragment may be removed from the peptide of interest prior to immunization by a variety of enzymatic or chemical means known in the art.

In some embodiments, nucleic acid sequences corresponding to these various C-terminal truncated C5a peptides (e.g., SEQ ID NOS:10, 11, 13, 17, 18, and 19) are used to generate recombinant DNA molecules that direct the expression of the C-terminal truncated C5a peptides in appropriate host cells, which are then purified and used as immunogens to generate the antibodies of the present invention. These DNA sequences may be included in any one of a variety of expression vectors for expressing C-terminal truncated C5a peptides in various hosts. Examples of vectors include, but are not limited to, chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies, and the like. Any vector may be used as long as it is replicable and viable in the host.

Large numbers of suitable vectors are known to those of skill in the art, and are commercially available. Such vectors include, but are not limited to, the following: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWLNEO, pSV2CAT, pOG44, PXT1, pSG (Stratagene) pSVK3, pBPV, pMSG, pSVL (Pharmacia). In general, mammalian expression vectors comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The DNA sequence in the expression vector may be operably linked to an appropriate expression control sequence(s) (promoter) to direct mRNA synthesis. Promoters useful in the present invention include, but are not limited to, the LTR or SV40 promoter, the *E. coli.* lac or trp, the phage lambda PL and PR, T3 and T7 promoters, and the CMV immediate early, HSV thymidine kinase, and mouse metallothionein-I promoters and other promoters known to control expression of peptides in prokaryotic or eukaryotic cells or their viruses. Recombinant expression vectors generally include origins of replication and selectable markers permitting transformation of the host cell (e.g., dihydrofolate reductase or neomycin resistance for eukaryotic cell culture, or such as tetracycline or ampicillin resistance in *E. coli*).

Transcription of the DNA encoding the C-terminal truncated C5a peptides of the present invention is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers. The expression vector may also contain a ribosome binding site for translation initiation and a transcription terminator.

Various host cells may be employed to recombinantly express the C-terminal truncated C5a peptides. Suitable host cells are higher eukaryotic cells (e.g., a mammalian or insect cell), lower eukaryotic cells (e.g., a yeast cell), and prokaryotic cells (e.g., a bacterial cell). Specific examples of host cells include, but are not limited to, *Escherichia coli, Salmonella typhimurium, Bacillus subtilis*, and various species within the genera Pseudomonas, Streptomyces, and Staphylococcus, as well as, *Saccharomycees cerivisiae, Schizosaccharomycees pombe*, Drosophila S2 cells, Spodoptera Sf9 cells, Chinese Hamster Ovary (CHO) cells, COS-7 lines of monkey kidney fibroblasts, (Gluzman, Cell, 23:175 [1981]), C127, 3T3, HeLa and BHK cell lines.

The constructs in host cells can be used in a conventional manner to produce the C-terminal truncated C5a peptides encoded by the recombinant sequences. In some embodiments, introduction of the construct into the host cell is effected by calcium phosphate transfection, DEAE-Dextran mediated transfection, or electroporation [Davis et al., Basic Methods in Molecular Biology, (1986)].

Following transformation of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification.

Methods for recovering and purifying C-terminal truncated C5a peptides from recombinant cell culture include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography (HPLC) can also be employed for final purification steps.

DNA sequences having coding sequences (e.g., SEQ ID NOS:10, 11, 13, 17, 18, and 19) fused in frame to a marker sequence allow for purification of the C-terminal truncated C5a peptide. One example is a histidine tag which may be supplied by a vector (e.g., a pQE-9 vector) which provides for purification of the polypeptide fused to the marker in the case of a bacterial host, or, for example, the marker sequence may be a hemagglutinin (HA) tag when a mammalian host (e.g., COS-7 cells) is used. The HA tag corresponds to an epitope derived from the influenza hemagglutinin protein (Wilson, et al., *Cell*, 37:767 [1984]).

The coding sequences for the C-terminal truncated C5a peptides can also be incorporated as a part of a fusion gene including a nucleotide sequence encoding a different polypeptide. One example employs the VP6 capsid protein of rotavirus used as an immunologic carrier protein for the C-terminal truncated C5a peptides, either in the monomeric form or in the form of a viral particle. The nucleic acid sequences corresponding to the various C5a peptides to which antibodies are to be raised can be incorporated into a fusion gene construct which includes coding sequences for a late vaccinia virus structural protein to produce a set of recombinant viruses expressing fusion proteins comprising C-terminal truncated C5a peptides as part of the virion. It has been demonstrated with the use of immunogenic fusion proteins utilizing the Hepatitis B surface antigen fusion proteins that recombinant Hepatitis B virions can be utilized in this role as well. Similarly chimeric constructs coding for fusion proteins containing C-terminal truncated C5a peptides and the poliovirus capsid protein are created to enhance immunogenicity of the set of polypeptide antigens [see e.g., EP Publication No. 025949; and Evans et al., *Nature* 339:385 (1989); Huang et al., *J. Virol*. 62:3855 (1988); and Schlienger et al., *J. Virol*. 66:2 (1992)]. The Multiple Antigen Peptide system for peptide-based immunization can also be utilized, wherein a desired C-terminal truncated C5a peptide sequence is obtained directly from organo-chemical synthesis of the peptide onto an oligomeric branching lysine core [see e.g., Posnett et al., *JBC* 263:1719 (1988) and Nardelli et al., *J. Immunol*. 148:914 (1992)]. C-terminal truncated C5a peptides can also be expressed and presented by bacterial cells in order to generate the antibodies of the present invention.

In addition to utilizing fusion proteins to enhance immunogenicity, fusion proteins can also facilitate the purification of proteins. Accordingly, the C5a peptides can be generated as a glutathione-S-transferase (GST) fusion protein. Such GST fusion proteins enable easy purification of the C5a peptides, such as by the use of glutathione-derivatized matrices [see e.g, *Current Protocols in Molecular Biology*, Eds. Ausabel et al., N.Y.: John Wiley & Sons, (1991)]. Also, a fusion gene coding for a purification leader sequence, such as a poly-(His)/enterokinase cleavage site sequence at the N-terminus of the desired C-terminal truncated C5a peptide, can allow purification of the expressed C-terminal truncated C5a fusion protein by affinity chromatography using, for example, a Ni2+ metal resin. The purification leader sequence can then be subsequently removed by treatment with enterokinase [see e.g., Hochuli et al., *J. Chromatography* 411:177 (1987)].

Techniques for making fusion genes are well known. Essentially, the joining of various DNA fragments coding for different polypeptide sequences is performed in accordance with conventional molecular biology techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. The fusion gene is synthesized by conventional techniques including automated DNA synthesizers. Alternatively, in other embodiments of the present invention, PCR amplification of gene fragments can be carried out using anchor primers which give rise to complementary overhangs between two consecutive gene fragments which is subsequently annealed to generate a chimeric gene sequence [see e.g., *Current Protocols in Molecular Biology*, Eds. Ausubel et al., John Wiley & Sons (1992)].

The C-terminal truncated C5a peptide sequences may be synthesized, whole or in part, using chemical methods well known in the art [see e.g., Caruthers et al., *Nuc. Acids Res. Symp. Ser*. 7:215–233 (1980); Crea and Horn, *Nuc. Acids Res*. 9:2331 (1980); Matteucci and Caruthers, *Tetrahedron Lett* 21:719 (1980); and Chow and Kempe, *Nuc. Acids Res*. 9:2807–2817 (1981)]. For example, C-terminal truncated C5a peptides can be synthesized by solid phase techniques, cleaved from the resin, and purified by preparative high performance liquid chromatography [see e.g., Creighton (1983) *Proteins Structures And Molecular Principles*, W H Freeman and Co, New York N.Y.]. In other embodiments of the present invention, the composition of the synthetic peptides may be confirmed by amino acid analysis or sequencing (see e.g., Creighton, supra).

Direct peptide synthesis can be performed using various solid-phase techniques [Roberge et al., *Science* 269:202–204 (1995)] and automated synthesis may be achieved, for example, using ABI 431A Peptide Synthesizer (Perkin Elmer, Norwalk Conn.) in accordance with the instructions provided by the manufacturer. Additionally the amino acid sequence of the C-terminal truncated C5a peptide sequences may be altered during direct synthesis yielding various C-terminal truncated C5a peptides which are used to generate the anti-C5a antibodies of the present invention.

Compounds mimicking the necessary conformation for generating the antibodies of the present invention are also contemplated as within the scope of the invention. For example, mimetics of the C-terminal truncated C5a peptides are contemplated. A variety of designs for such mimetics are possible. For example, cyclic C-terminal truncated C5a peptides, in which the necessary conformation for immunogenicity is stabilized by non-peptides, are specifically contemplated (See e.g. U.S. Pat. No. 5,192,746 to Lobl, et al., U.S. Pat. No. 5,169,862 to Burke, Jr., et al., U.S. Pat. No. 5,539,085 to Bischoff, et al., U.S. Pat. No. 5,576,423 to Aversa et al., U.S. Pat. No. 5,051,448 to Shashoua, and U.S. Pat. No. 5,559,103 to Gaeta et al., all of which describe muliple methods for creating such compounds). The present invention also contemplates non peptide compounds that mimic C-terminal truncated C5a peptides, as well as multimeric compounds that repeat the relevant peptide sequences.

TABLE 1

C5a Sequences and Peptides Useful in Generating Antibodies

| Species | SEQ ID NO: | Amino Acid Sequence |
| --- | --- | --- |
| Rat C5a (full seq.) | SEQ ID NO:1 | DLQLLHQKVEEQAAKYKHRVP KKCCYDGARENKYETCEQRVA RVTIGPHCIRAFNECCTIADKIR KESHHKGMLLGR |
| Rat C5a (residues 17–36) | SEQ ID NO:2 | KHRVPKKCCYDGARENKYET |
| Human C5a (full seq.) | SEQ ID NO:3 | MLQKKIEEIAAKYKHSVVKKCC YDGASVNNDETCEQRAARISLG PRCIKAFTECCVVASQLRANISH KDMQLGR |
| Human C5a (res. 1–20) | SEQ ID NO:4 | MLQKKIEEIAAKYKHSVVKK |
| Human C5a (res. 21–40) | SEQ ID NO:5 | CCYDGASVNNDETCEQRAAR |
| Human C5a (res. 55–74) | SEQ ID NO:6 | CVVASQLRANISHKDMQLGR |
| Human C5a (res. 12–20) | SEQ ID NO:14 | KYKHSVVKK |
| Human C5a (res. 28–33) | SEQ ID NO:15 | VNNDET |
| Human C5a (res. 38–46) | SEQ ID NO:16 | AARISLGPR |
| Bovine C5a (full seq.) | SEQ ID NO:7 | MLKKKIEEEAAKYRNAWVKKC CYDGAHRNDDETCEERAARIAI GPECIKAFKSCCAIASQFRADEH HKNMQLGR |
| Porcine C5a (full seq.) | SEQ ID NO:8 | MLQKKIEEEAAKYKYAMLKKC CYDGAYRNDDETCEERAARIKI GPKCVKAFKDCCYIANQVRAEQ SHKNIQLGR |

TABLE 2

Rat and Human C5a Polynucleotide Sequences Useful in Generating C5a Peptides

| Species | SEQ ID NO: | Polynucleotide Sequence |
| --- | --- | --- |
| Human C5a (full seq.) | SEQ ID NO:9 | GATCCAGTATGTTGCAAAAAA AAATTGAAGAAATTGCTGCTA AATATAAACATTCTGTTGTTAA AAAATGTTGTTATGATGGAGCT TCTGTTAATAATGATGAAACCT GCGAACAACGCGCTGCTAGAA TTTCTTTGGGACCTAGATGTA TTAAAGCATTTACAGAATGTTG TGTTGTTGCTTCTCAATTGAG GCGAATATTTCTCATAAAGATA TGCAATTGGGAAGATAGGATC CGTCGA |
| Human C5a (for res. 1–20) | SEQ ID NO:10 | ATGTTGCAAAAAAAAATTG AAGAAATTGCTGCTAAATA TAAACATTCTGTTGTTAAAAAA |
| Human C5a (for res. 21–40) | SEQ ID NO:11 | TGTTGTTATGATGGAGCTTC TGTTAATAATGATGAAACCT GCGAACAACGCGCTGCTAGA |
| Human C5a (for res. 12–20) | SEQ ID NO:17 | TTGCTGCTAAATATAAACAT TCTGTTG |
| Human C5a (for res. 28–33) | SEQ ID NO:18 | GAGCTTCTGTTAATAATG |
| Human C5a (for res. 38–46) | SEQ ID NO:19 | AACAACGCGCTGCTAGAATT TCTTTGG |
| Rat C5a (full seq.) | SEQ ID NO:12 | GACCTGCAGCTCCTGCATCAG AAAGTGGAAGAACAAGCTGCT AAATACAAACACCGTGTGCCC AAGAAATGCTGTTATGATGGA GCCCGAGAAAACAAATACGAA ACCTGTGAGCAGCGAGTTGCC CGGGTGACCATAGGCCCACAC TGCATCAGGGCCTTCAACGAG |

TABLE 2-continued

Rat and Human C5a Polynucleotide
Sequences Useful in Generating C5a Peptides

| Species | SEQ ID NO: | Polynucleotide Sequence |
|---|---|---|
| Rat C5a (for res. 17–36) | SEQ ID NO:13 | TGTTGTACTATTGCGGATAAG<br>ATCCGAAAAGAAAGCCACCAC<br>AAAGGCATGCTGTTGGGAAGG<br>AAACACCGTGTGCCCAAGAAA<br>TGCTGTTATGATGGAGCCCGA<br>GAAAACAAATACGAAACC |

TABLE 3

Variant C-Terminal Truncated
C5a Peptide Sequences

| SEQ ID NO: | Amino Acid Sequence |
|---|---|
| SEQ ID NO:20 | KYKHTVVKK |
| SEQ ID NO:21 | KYKHSAVKK |
| SEQ ID NO:22 | KYKHSAAKK |
| SEQ ID NO:23 | KYKHSVAKK |
| SEQ ID NO:24 | VNNQET |
| SEQ ID NO:25 | VNNDES |
| SEQ ID NO:26 | VNNQES |
| SEQ ID NO:27 | ANNDET |
| SEQ ID NO:28 | AARISIGPR |
| SEQ ID NO:29 | AARISVGPR |
| SEQ ID NO:30 | AARITLGPR |
| SEQ ID NO:31 | AVRISLGPR |
| SEQ ID NO:32 | VARISLGPR |
| SEQ ID NO:33 | VVRISLGPR |
| SEQ ID NO:34 | MLQKKIEEIAAKYKHSVVK |
| SEQ ID NO:35 | MLQKKIEEIAAKYKHSVV |
| SEQ ID NO:36 | MLQKKIEEIAAKYKHSV |
| SEQ ID NO:37 | MLQKKIEEIAAKYKHS |
| SEQ ID NO:38 | MLQKKIEEIAAKYKH |
| SEQ ID NO:39 | LQKKIEEIAAKYKHSVVKK |
| SEQ ID NO:40 | QKKIEEIAAKYKHSVVKK |
| SEQ ID NO:41 | KKIEEIAAKYKHSVKKK |
| SEQ ID NO:42 | KIEEIAAKYKHSVVKK |
| SEQ ID NO:43 | IEEIAAKYKHSVVKK |
| SEQ ID NO:44 | MIQKKIEEIAAKYKHSVVKK |
| SEQ ID NO:45 | MVQKKIEEIAAKYKHSVVKK |
| SEQ ID NO:46 | MLDKKIEEIAAKYKHSVVKK |
| SEQ ID NO:47 | MLQKKIEEIAAKYKHTVVKK |
| SEQ ID NO:48 | MLQKKIEEIVAKYKHSVVKK |
| SEQ ID NO:49 | MLQKKIEEIVVKYKHSVVKK |
| SEQ ID NO:50 | MLQKKIEEIAAKYKHSVAKK |
| SEQ ID NO:51 | MLQKKIEEIAAKYKHSAAKK |
| SEQ ID NO:52 | MLQKKIEEIAAKYKHSAVKK |
| SEQ ID NO:53 | MLQKKIEEIAVKYKHSVVKK |
| SEQ ID NO:54 | CCYDGASVNNDETCEQRAA |
| SEQ ID NO:55 | CCYDGASVNNDETCEQRA |
| SEQ ID NO:56 | CCYDGASVNNDETCEQR |
| SEQ ID NO:57 | CCYDGASVNNDETCEQ |
| SEQ ID NO:58 | CCYDGASVNNDETCE |
| SEQ ID NO:59 | CYDGASVNNDETCEQRAAR |
| SEQ ID NO:60 | YDGASVNNDETCEQRAAR |
| SEQ ID NO:61 | DGASVNNDETCEQRAAR |
| SEQ ID NO:62 | GASVNNDETCEQRAAR |
| SEQ ID NO:63 | ASVNNDETCEQRAAR |
| SEQ ID NO:64 | CCYQGASVNNDETCEQRAAR |
| SEQ ID NO:65 | CCYDGASVNNQETCEQRAAR |
| SEQ ID NO:66 | CCYQGASVNNQETCEQRAAR |
| SEQ ID NO:67 | CCYDGASVNNDESCEQRAAR |
| SEQ ID NO:68 | CCYDGATVNNDETCEQRAAR |
| SEQ ID NO:69 | CCYDGVSVNNDETCEQRAAR |
| SEQ ID NO:70 | CCYDGASANNDETCEQRAAR |
| SEQ ID NO:71 | CCYDGASVNNDETCEQRVAR |
| SEQ ID NO:72 | CCYDGASVNNDETCEQRVVR |
| SEQ ID NO:73 | CCYDGASVNNDETCEQRAVR |
| SEQ ID NO:74 | CCYDGVSANNDETCEQRVVR |

In one embodiment, the present invention contemplates a method of producing polyclonal antibodies, comprising; providing an animal and an immunogenic composition, wherein the composition comprises C-terminal truncated C5a peptides; and immunizing the animal with the immunogenic composition in order to generate antibodies. It is not intended that the present invention be limited to particular C-terminal truncated peptides. A variety of C-terminal truncated peptides are contemplated. In one embodiment, the C-terminal truncated peptide corresponds to the entire N-terminal region of C5a peptide. In another embodiment, the C-terminal truncated peptide is a fragment or portion of the N-terminal region of C5a peptide. In another embodiment, the fragment or portion of the N-terminal region of C5a peptide is between approximately 5 and approximately 50 amino acids in length. In some embodiments, the C-terminal truncated peptide is fifty amino acids in length. In other embodiments, the C-terminal truncated peptides are approximately five amino acids in length. In preferred embodiments, the C-terminal truncated peptides are approximately 20 amino acids in length. In especially preferred embodiments, the C-terminal truncated peptides are selected from SEQ ID NOS:2, 4, and 5.

III. Antibody Applications

A. Prophylactic use in Humans

The diagnosis of sepsis is problematic. First, the development of sepsis does not require the persistent release of toxin(s), nor the presence of organisms, in the circulation. Thus, many patients who die of sepsis are never shown to be bactermic. [R. C. Bone, Ann. Intern. Med. 115:457–469 (1991)]. Second, even if bacteria are detected, the amount of time needed for this detection is often too great to be practical.

For these reasons and others, the present invention contemplates the use of anti-C5a antibodies in humans prior to the onset of symptoms (e.g., prophylactically). In particular, the present invention contemplates the use of anti-C5a antibodies as prophylactic treatment in patients at high risk for infection, as well as sepsis.

High risk patients include surgical patients (particularly the elderly), low birth weight infants, burn victims and trauma patients. Trauma patients are particularly difficult to examine because of the multitude of invasive procedures that they have undergone. Trauma patients are also typically hooked up to a number of devices, including intravascular lines, mechanical ventilators and Foley catheters. While every attempt is made to change intravascular lines, this is frequently impossible because of the extent of trauma and the lack of venous accessibility. [E. S. Caplan and N. Hoyt, Am. J. Med. 70:638–640 (1981)].

Most patients with multiple trauma have fever, as well as increased white cell counts due to the stress of the trauma itself. The classic indicators of infection, therefore, may or may not reflect an ongoing infection.

Because of this, current clinical practice involves treating patients with antibiotics only for specific indications, and for as short a period of time as possible. Generally, the average course for any documented infection is seven to ten days. Prophylactic antibiotics are used in only three instances: open fractures, penetrating abdominal injuries and penetrating facial injuries in which there is injury to the respiratory mucosa. Even in these situations, antibiotics are used for only three to five days, depending on the injury.

Burn patients have many problems with respect to the diagnosis and therapy for infection. Since the magnitude of thermal injury is related to the level of trauma in a burn victim, this becomes even more of a problem with acute cases. It is reported that septicemia appears in the blood cultures of burn patients almost four days after a septic state. [M. Meek et al., *J. Burn Care Rehab.* 12:564–568 (1991)]. Consequently, therapy with the antibodies of the present invention is particularly appropriate immediately after the burn injury as a means of preventing a septic reaction. Furthermore, in severe cases, consideration should be given to the topical administration of the antibodies of the present invention to prevent wound sepsis.

Finally, surgical patients also represent a risk group where the antibodies of the present invention can be used successfully. Current practice involves the prophylactic use of antibiotics in a very narrow category of cases (e.g., elective colorectal procedures, cholecystectomy, hysterectomy and Caesarean sections). [R. L. Nichols in *Decision Making in Surgical Sepsis*, B. C. Decker, Inc., Philadelphia, pp. 20–21 (1991)]. One to two grams of a broad-spectrum antibiotic are administered intravenously at the induction of anesthesia. An additional dose may be given during an extensive procedure or post-operatively but prophylaxis beyond 24 hours is not indicated. Twenty-four hours of antibiotic prophylaxis is considered to be sufficient to control contamination. Continuance of antibiotic prophylaxis beyond 24 hours is an added expense, particularly when using an antibiotic with short serum and tissue half-lives. Most importantly, continuation of antibiotic prophylaxis also runs an excessive risk of drug toxicity and emergence of resistant strains. As such, the present invention contemplates the use of anti-C5a antibodies to help reduce the need for antibiotics, and reduce the risk of sepsis.

In this regard, the present invention contemplates a method comprising; providing; a subject at risk for sepsis, and a therapeutic composition comprising an antibody specific for complement component C5a peptide, and prophylactically administering said therapeutic composition to the subject. In some embodiments administering the composition prevents the onset of symptoms of sepsis.

B. Acute Therapy in Humans

The present invention also contemplates the use of anti-C5a antibodies in a therapeutic preparation for acute treatment. In this case, treatment involves administration of the antibodies after infection is detected and/or sepsis is suspected.

Evidence suggestive of infection includes the following: (1) core temperature higher than 38° C. or lower than 35° C.; (2) peripheral blood leukocyte count greater than $12 \times 10^9$/L or less than $3 \times 10^9$/L (not due to chemotherapy), or at least 20% immature forms; (3) growth of gram-negative organisms from a blood culture drawn within the preceding 48 hours; or (4) documented or suspected site of gram-negative infection.

A systemic septic reaction is characterized by at least one of the following: arterial hypotension (systolic blood pressure <90 mm Hg or an acute drop of 30 mm Hg); metabolic acidosis (base deficit >5 mEq/L); decreased systemic vascular resistance (systemic vascular resistance <800 dynes/s·cm$^5$); tachypnea (respiratory rate >20/min or ventilation >10 L/min if mechanically ventilated); or otherwise unexplained dysfunction of the kidney (urine output <30 ml/h), or lungs.

It must be stressed that the anti-C5a antibodies of the present invention should ideally be used prior to a systemic infection, if possible. For example, the antibodies are administered immediately after bacteremia or fungemia is detected. Similarly, antibodies can be administered where there is an obvious sign of infection at a particular site (e.g., wounds, sinusitis, meningitis, respiratory, gastrointestinal, or urinary tract infections, etc.).

Primary bacteremia is typically defined as two or more blood cultures with the same bacterial organism occurring in a patient with no other obvious site of infection. Sinusitis is diagnosed in a patient who has at least two of the following: purulent nasal discharge, roentgenographic evidence of sinusitis or purulent material aspirated from the sinuses.

The lower respiratory tract is a common site of infection. Pneumonia in the intubated patient is diagnosed in a patient when there is fever, leukocytosis and a Gram stain with many polymorphonuclear leukocytes. Pneumonia may also be diagnosed in a patient with a new infiltrate that has not cleared with intensive physical therapy (this last criterion helps rule out atelectasis).

The C5a peptide has been implicated in the pathogenesis of bacterial meningitis [Stahel, et al., *J. Immunol.* Jul. 15;159(2):861–9 (1997)]. As such, treatment of acute meningitis with the anti-C5a antibodies of the present invention is contemplated. Among the bacterial causes of meningitis, two gram-negative organisms (*Neisseria meningitidis* and *Haemophilus influenzae*), and one gram-positive organism (*Streptococcus pneumoniae*), are the major culprits. *N. meningitidis* is responsible for an estimated 24–25% of meningitis in children one month of age through 15 years; for adults, the figure is 10–35%. *H. influenzae* is responsible for an estimated 40–60% of meningitis cases in children one month of age through 15 years, while *S. pneumoniae* is responsible for 10–20% of meningitis cases in the same age group, as well as 30–50% of cases in adults (over 15 years). [W. K. Joklik et al. (eds.), *Zinsser Microbiology*, 18th ed., p. 485, Appleton-Century-Crofts, Norwalk, Conn. (1984).] Other organisms such as Streptococcus spp. in groups A and B, *Staphylococcus aureus, Listeria monocytogenes*, and various gram-negative bacilli (e.g., enterics such as *E. coli*) are responsible for sporadic cases. Untreated, bacterial meningitis is fatal in 70–100% of patients, and infected neonates may have motor or intellectual impairment related to their infection. [J. M. Slack and I. S. Snyder, *Bacteria and Human Disease*, pp. 128–133, Yearbook Medical Publishers (1978).]

The blood-brain barrier represents a significant obstacle to treatment of meningitis, especially prophylactically. As the barrier is designed to prevent invasion of organisms and uptake of compounds (e.g., antimicrobials), intravenous antimicrobial administration is not always sufficient. For example, estimates provided in experimental studies indicate that drug concentrations in the cerebrospinal fluid and brain are approximately $\frac{1}{200}$ to $\frac{1}{500}$ of those in serum. [G. P. Youmans et al., *Biologic and Clinical Basis of Infectious Diseases*, 3d ed., p. 553, W. B. Saunders Co., (1985).] Even with the inflammatory changes associated with an intensity characteristic of bacterial meningitis, passage of antimicrobials is hindered by the barrier. [Id.]

Endotoxemia due to the release of endotoxins from dividing organisms and the presence of endotoxin in the cerebrospinal fluid (CSF) present serious complications during sepsis and meningitis. Endotoxin is detectable in the plasma and CSF of patients with meningitis due to gram-negative bacteria. (Awad et al., supra at 560.) Perhaps due to increased permeability of the bowel mucosa, endotoxin may also be found in the plasma of patients with meningitis due to gram-positive organisms (e.g., *Streptococcus pneumoniae*).

Ironically, release of endotoxin is aggravated by antimicrobial treatment. Indeed, it is believed that aggressive antibiotic treatment can be life-threatening. This is due to the increased burden of endotoxin present in the blood and CSF which results when a large number of organisms are simultaneously killed by the antibiotic. This increased endotoxin burden results in the pathology associated with fatal meningitis and is a significant problem facing clinicians who must treat a seriously ill patient within the first few hours of disease.

Therefore, the present invention contemplates treating acute septic conditions with anti-C5a antibodies. It is contemplated that these antibodies be administered alone, or in combination with other therapeutic preparations. In preferred embodiments, the present invention provides a method comprising; providing; a subject suffering from symptoms of sepsis, a therapeutic composition comprising an antibody specific for complement component C5a peptide, and administering the therapeutic composition to the subject.

C. Veterinary Care

Septicemia and sepsis are by no means limited to human beings. Infection by gram-negative bacteria accounts for significant morbidity and mortality in neonatal livestock, such as calves. [D. D. Morris et al., *Am. J. Vet. Res.* 47:2554–2565 (1986).]Interestingly, humoral immune status is again related to susceptibility to sepsis and this is largely dependent on passive transfer from colostrum. For this reason, in some embodiments the present invention contemplates determining the immune status of the animal prior to administration of the anti-C5a antibodies. This determination can be made by screening neonatal calves for total circulating serum immunoglobulin (e.g., by ELISA).

Where the immune status is poor (e.g., low total IgG levels), the antibodies of the present invention should be used prophylactically. Where the animal's immune status is healthy, use of the antibodies may be needed for acute therapy of gram-negative bacterial sepsis, which remains prevalent in neonatal calves even with high natural antibody levels.

The present invention contemplates the treatment of other animals as well. For example, among foals less than 10 days of age in critical distress, sepsis is the most serious problem. [A. M. Hoffman et al., *J. Vet. Int. Med.* 6:89–95 (1992).] Symptoms highly indicative of sepsis risk include weakness, metabolic disturbance and dehydration. In one embodiment, the invention contemplates using antibodies for prophylactic treatment of foals less than 10 days of age having these indicators, or those at risk of infection.

While positive blood cultures are found in less than half of the cases, those animals found positive have a very poor chance of survival. The present invention therefore contemplates using anti-C5a antibodies for acute treatment of any animal with evidence of septicemia, with or without culture-proven cases.

IV. Therapeutic Preparations and Combinations

In some embodiments, the present invention contemplates using therapeutic compositions of soluble anti-C5a antibodies. It is not intended that the present invention be limited by the particular nature of the therapeutic composition. For example, such compositions can be provided together with physiologically tolerable liquids, gels, solid carriers, diluents, adjuvants and excipients (and combinations thereof). In addition, anti-C5a antibodies may be used together with other therapeutic agents, including other immunoglobulins or antibiotics.

As noted above, these therapeutic compositions can be administered to mammals for veterinary use, such as with domestic animals, and clinical use in humans in a manner similar to other therapeutic agents. In general, the dosage required for therapeutic efficacy varies according to the type of use and mode of administration, as well as the particularized requirements of individual hosts. The attending medical professional is capable of determining the therapeutically effective dosage based on the characteristics of the subject (e.g. gender, age, weight, etc.)

With respect to the mode of administration, in some embodiments the antibodies are administered intravenously, intramuscularly, subcutaneously, intradermally, intraperitoneally, intrapleurally, intrathecally, or topically. In some embodiments, formulations for such administrations may comprise an effective amount of anti-C5a antibodies in sterile water or physiological saline.

On the other hand, formulations may contain such normally employed additives as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions typically contain 1%–95% of active ingredient, preferably 2%–70%.

The compositions are preferably prepared as injectables, either as liquid solutions or suspensions; solid forms suitable for solution in, or suspension in, liquid prior to injection may also be prepared.

The antibodies of the present invention are often mixed with diluents or excipients which are compatible and physiologically tolerable. Suitable diluents and excipients are, for example, water, saline, dextrose, glycerol, or the like, and combinations thereof. In addition, if desired, the compositions may contain minor amounts of auxiliary substances such as wetting or emulsifying agents, stabilizing or pH buffering agents.

Where repeated administrations are required, it may be beneficial to first clear any anti-hapten antibodies by administering free antibiotic. This can then be followed by administration of the anti-C5a antibodies of the present invention.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); $\mu$M (micromolar); mol (moles); mmol (millimoles); $\mu$mol (micromoles); nmol (nanomoles); pmol (picomoles); g (grams); mg (milligrams); $\mu$g (micrograms); ng (nanograms); 1 or L (liters); ml (milliliters); $\mu$l (microliters); cm (centimeters); mm (millimeters); $\mu$m (micrometers); nm (nanometers); ° C. (degrees Centigrade); Sigma (Sigma Chemical Co., St. Louis, Mo.).

EXAMPLE 1

Induction of Sepsis in Rats by Cecal Ligation Puncture

This Examples describes the induction of sepsis by Cecal Ligation Puncture (CLP) in Male Long-Evans specific pathogen-free rats (275–300 mg) obtained from Harlan, Inc., Indianapolis, Indiana. Anesthesia was induced by intraperitoneal administration of ketamine (20 mg/100 mg body weight). Through a 2 cm abdominal midline incision the cecum was ligated below the ileocecal valve without obstructing the ileum or colon. The cecum was then subjected to a single "through and through" perforation with a 21-gauge needle. After repositioning the bowel, the abdominal incision was closed in lagers with plain gut surgical suture 4-0 (Ethicon, Inc., Somerville, N.J.) and metallic clips. Sham animals underwent the same procedure except for ligation and puncture of the cecum.

EXAMPLE 2

Preparation and Characterization of Anti-Rat C5a Antibodies

This Example describes the preparation and characterization of anti-rat C5a antibodies. Rat C5a peptide with the sequence KHRVPKKCCYDGARENKYET (SEQ ID NO:2) was obtained from Research Genetics (Huntsville Ala.) and coupled to keyhole limpet hemocyanin (KLH). This 20-mer rat C-terminal truncated C5a peptide corresponds to amino acid residues 17–36 of the full length rat C5a peptide [Rothermel, E. et al., *Biochimica. et Biophysica. Acta.* 1351:9–12, (1997)], which is listed as SEQ ID NO:1. The coupled peptide was used as an antigen to immunize rabbits. After several injections, the antibody was affinity purified using the synthetic 20-mer peptide coupled to beads. Immunoprecipitation with activated rat serum using beads coupled with this antibody yielded a single band with a 14 kDa position in Western blot analysis, characteristic of rat C5a peptide [See, Ward, P. A. and Becker, E. L., *J. Exp. Med.* 127:693–709 (1968)].

When added at a concentration of 100 µg/ml, the antibody did not affect whole hemolytic complement activity (CH50) of fresh rat serum. Addition of 0, 10, 20, 40, 80 micrograms of anti-C5a Ab yielded CH50 values of 99, 94, 91, 93, and 94 units/ml. Therefore, the fact that CH50 levels are not affected by the anti-C5a antibodies indicates that the anti-C5a antibodies are effective without compromising the entire complement system (including the classical and alternate pathways).

EXAMPLE 3

Anti-Rat C5a Antibodies Prevent Sepsis

This Example describes the treatment of sepsis. CLP-induced sepsis was generated in three different groups of rats according to the procedure of Example 1 above. The first group (n=21) was treated intravenously with 400 µg of preimmune IgG (in a volume of 300 µg) immediately after the CLP procedure. The second group (n=10) was treated intravenously with 400 µg of anti-C5a IgG prepared according to Example 2 above (in a volume of 300 µg) immediately after the CLP procedure. The third group (n=12) was depleted of C3 by four intraperitoneal injections of purified cobra venom factor (25 units per injection at 12 hour intervals) during the 48 hour period prior to induction of CLP. This protocol has been shown to reduce serum C3 levels to less than 3% of normal and to suppress whole complement hemolytic activity (CH50) to undetectable levels [Hill, J. H. and Ward, P. A., *J. Exp. Med.* 133:885–900, (1971)].

Survival rates for the three groups of rats were determined over a ten-day period, with assessment every 6 hours. A sham operated group of rats (n=10) in which no cecal puncture was performed, were also included in this study and all survived during the 10 day period.

All animals had unlimited access to food and water, both pre- and postoperatively. Survival data for the three CLP treated groups is depicted in FIG. 1. In the CLP group receiving preimmune IgG, survival was 66.7% (14/21) 24 hours after CLP, diminishing progressively each day until day 8, at which time only 9.5% (2/21) were alive. In the C3 depleted group, the survival time was greatly reduced, with all animals dead before day 4.5. When this group was compared to the CLP group receiving preimmune IgG, the outcomes were statistically different (p=0.01 by the Chi square test). In the CLP group receiving anti-C5a antibodies, survival times were dramatically improved. By day 5, 50% of the animals survived, and no additional deaths were observed in the next 5 days. When the CLP group receiving preimmune IgG was compared to the group receiving anti-C5a IgG, the p values for 10 day survival were 0.012 and 0.022 by Chi Square Test and Fisher's exact test respectively. Comparing the outcome of the CLP group receiving anti-C5a antibodies to the CLP group depleted of C3, p equaled 0.01 according to the Chi square test.

EXAMPLE 4

Anti-Rat C5a Antibodies Reduce Bacteremia in Septic Rats

This Example describes the in vitro detection and reduction of bacteremia in septic rats. CLP-induced sepsis was generated in two different groups of rats according to the procedure of Example 1 above. One group (n=5) was treated intravenously with 400 µg of preimmune IgG, which was infused immediately after surgery. The second group (n=5) was treated intravenously with 400 µg of anti-C5a IgG (prepared according to Example 2), which was infused immediately after surgery. A third group of sham operated rats (n=5) in which no cecal puncture was performed, were also included.

Figure 2:
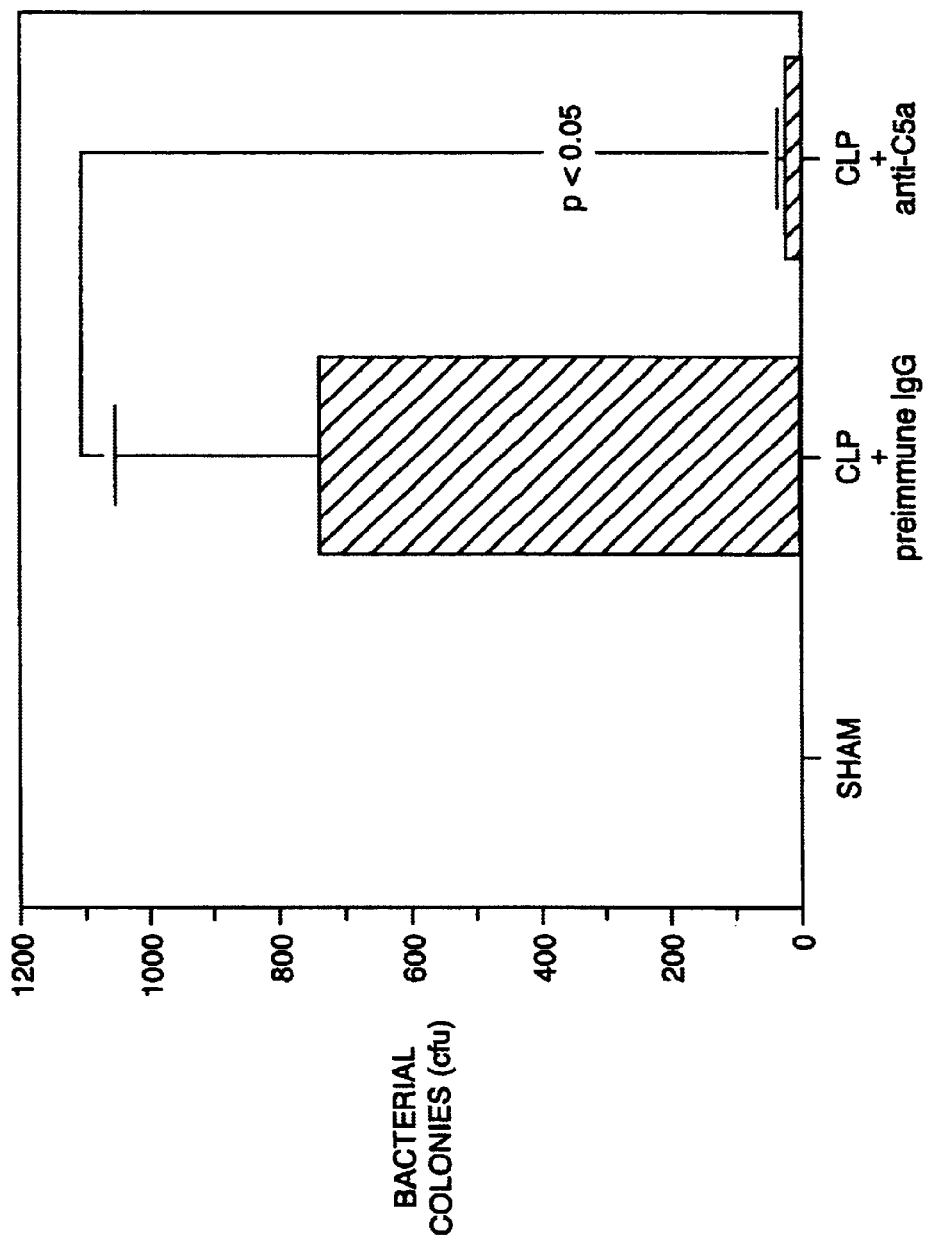
FIG. 2 shows a graph demonstrating the ability of anti-C5a antibodies to reduce bacteria blood of septic rats.

CLP-induced sepsis in rats is known to be associated with the development of bacteremia involving the presence of both aerobic and anaerobic bacteria in the blood [Deitch, E. A. *Schock* 9:1–11, (1997)]. Blood samples were obtained from these three groups 36 hours after sham surgery or induction of CLP. This was done by drawing blood via the posterior vena cava after topical treatment of the puncture site with iodine swabsticks (Professional Disposables, Inc., Orangeburg, N.Y.). Blood samples were placed in Isolator Microbial Tubes (Wampole, Inc.) and cultured on chocolate sheep blood agar plates (incubated aerobically in 5% $CO_2$) or on lysed blood agar plates (incubated anaerobically). All plates were incubated for 96 hours prior to determination of colony counts (cfu). The presence of aerobic and anaerobic bacteria in blood was measured as cfu is shown in FIG. 2.

In the sham operated group at 36 hours, cfu were not detectable. In the CLP group receiving preimmune IgG, the cfu value (x±SEM) was 740±328, while in the CLP group treated with anti-C5a antibodies, the cfu value was profoundly reduced, by 98% (p<0.05), to 18±10 cfu. When subcultures of mixed aerobic or anaerobic bacteria obtained from the blood of CLP rats incubated in the presence of either preimmune IgG or anti-C5a IgG (each at 100 µg/ml), no reduction in cfu values were found, indicating that anti-C5a antibodies are not directly bacteriostatic.

Figure 3:
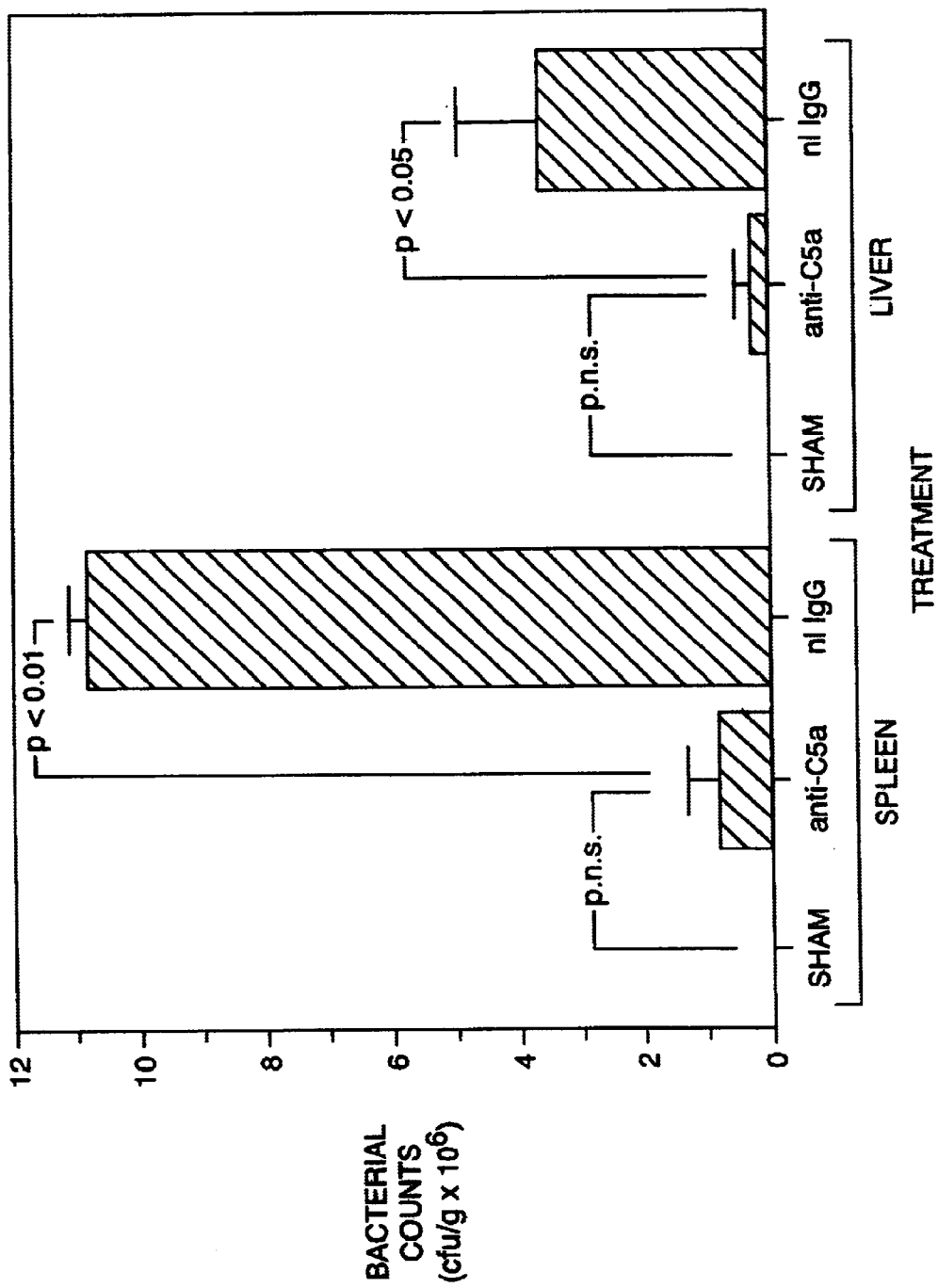
FIG. 3 shows a graph demonstrating the ability of anti-C5a antibodies to reduce bacteria in the organs of septic rats.

Bacteremia was also assayed in the organs of both sham and CLP treated rats, which received either preimmune IgG or anti-C5a antibodies (prepared according to Example 2). Livers and spleens were obtained from these rats 36 hours after surgery. These tissues were homogenized and cfu/g of tissue was determined using procedures similar to those used for the blood samples described above. The data is shown in FIG. 3, in which the cfu values for aerobic and anaerobic bacteria were arbitrarily aggregated. In all cases, there was a 1:1 ratio of these two classes of bacteria. In sham animals and in CLP animals treated with anti-C5a IgG, the cfu values were low in both liver and spleen. Between these two groups and in both organs, there were no statistically significant differences in cfu values. In marked contrast, CLP rats treated with preimmune IgG had very high cfu values ($3-11\times10^6$/g tissue).

EXAMPLE 5

Anti-Rat C5a Antibody Reduces C5a Binding to Neutrophils

This Example describes the binding of C5a peptide to neutrophils in the blood of septic rats, and ability of anti-rat C5a antibodies to reduce this binding. Blood neutrophils were obtained from both sham and CLP treated rats, which received either preimmune IgG or anti-C5a antibodies (prepared according to Example 2) at 12, 24 and 36 hours after CLP. Neutrophils were evaluated in flow cytometry for the surface content of C5a peptide using the procedure described below.

Whole blood was recovered from these rats, being drawn into syringes containing the anticoagulant ACD (Baxter Health Care Corp., Deerfield, Ill.). Duplicate aliquots (250 µl) of cells were incubated with an equal volume of phosphate buffered saline. The phosphate buffer, pH 7.4, was made up with heat inactivated 1% fetal bovine serum and 0.1% $NaN_3$, containing 10 µg/ml of either anti-rat C5a polyclonal antibody (as used in Mulligan, M. S. et al., *J. Clin. Invest.* 98:503–512, 1996) or irrelevant rabbit IgG control antibody (Jackson Laboratories, Ban Harbor, Me.). The cells were incubated at 5° C. for 30 minutes. Cells were washed once and red blood cells lysed with FACS solution (Becton Dickinson, San Jose, Calif.). Cells were then washed and incubated with phycoerythrin labeled anti-rabbit IgG (Sigma Chemical Co., St. Louis, Mo.). Cells were washed twice and suspended in 400 µl PBS containing 2% paraformaldehyde. Phycoerythrin intensity of gated populations (identified as forward versus side scatter light) was measured on a FACScan Flow Cytometry System (Becton Dickinson) in which 10,000 cells per gate were counted and the amount of phycoerythrin analyzed using PC-LYSYS software (Becton Dickson).

The data collected from this procedure is shown in Table 3. Mean channel fluorescence (MCF) values for neutrophils obtained from sham operated rats or from CLP rats at 12 hours showed very low MCF values for C5a peptide. By 24 and 48 hours, neutrophils from CLP animals showed nearly 4 fold increases in binding of anti-C5a IgG, suggesting that these cells contained substantial amounts of C5a on their surfaces. Binding of preimmune IgG to neutrophils from CLP rats at 24 and 36 hours was very low (less than 10 MCF units). Thus, during CLP induced sepsis, blood neutrophils acquire C5a peptides on their surfaces. When C5a peptide content was evaluated on blood neutrophils obtained from CLP rats pre-treated with 400 µg anti-C5a, there were consistent reductions in C5a content at 24 and 36 hours when compared to neutrophils from CLP rats pre-treated with preimmune IgG.

TABLE 3

Detection by Flow Cytometry of C5a Peptides on Blood Neutrophils During Sepsis

| | Mean Channel Fluorescence (mean ± SEM) | | | |
|---|---|---|---|---|
| Group | 0 hour | 12 hour | 24 hour | 36 hour |
| Sham | 12.8 ± 1.48* | | | |
| CLP + preimmune IgG (400 µg) | | 11.9 ± 0.54 | 43.5 ± 1.42 | 45.6 ± 0.64 |
| CLP + anti-C5a IgG (400 µg) | | 10.6 ± 0.37 | 32.6 ± 0.34 | 32.3 ± 2.74 |

*All displayed binding values represent results with rabbit anti-C5a IgG as detected with phycoerythrin labeled anti-rabbit IgG. The binding value of preimmune IgG was 4.45 ± 0.16. For each data point, n = 4 and all samples were analyzed in quadruplicate.

EXAMPLE 6

Anti-Rat C5a Antibody Preserves $H_2O_2$ Production in Septic Rat Neutrophils This Example describes the ability of anti-rat C5a antibody to preserve the $H_2O_2$ production of neutrophils from septic rats. Blood neutrophils were obtained from both sham and CLP treated rats, which received 400 µg of either preimmune IgG or anti-C5a antibodies (prepared according to Example 2) 36 hours after CLP or sham surgery. Neutrophil generation of $H_2O_2$ was assayed using the procedure described below.

Neutrophils were isolated from blood using dextran sedimentation and hypotonic red blood cell lysis. $7.5\times10^5$ cells were suspended in Hank's balanced salt solution (in a final volume of 1.0 ml) in the presence or absence of catalase (100 units/ml) in a final volume of 1.0 ml. Neutrophils were then stimulated for 1 hour at 37° with phorbol myristate acetate (PMA) at a concentration of 100 ng/ml. Stimulation was terminated by addition of 10% (vol/vol) trichloroacetic acid. After removing precipitated protein by centrifugation (10 minutes at 500×g), 10 mM ferrous ammonium sulfate (0.2 ml) and 2.5 M potassium thiocyanate (0.1 ml) were added to the sample. The presence of the ferrithiocyanate complex formed in the presence of peroxide was measured at 480 nm and compared to a standard curve generated using dilutions of stock $H_2O_2$.

Figure 4:
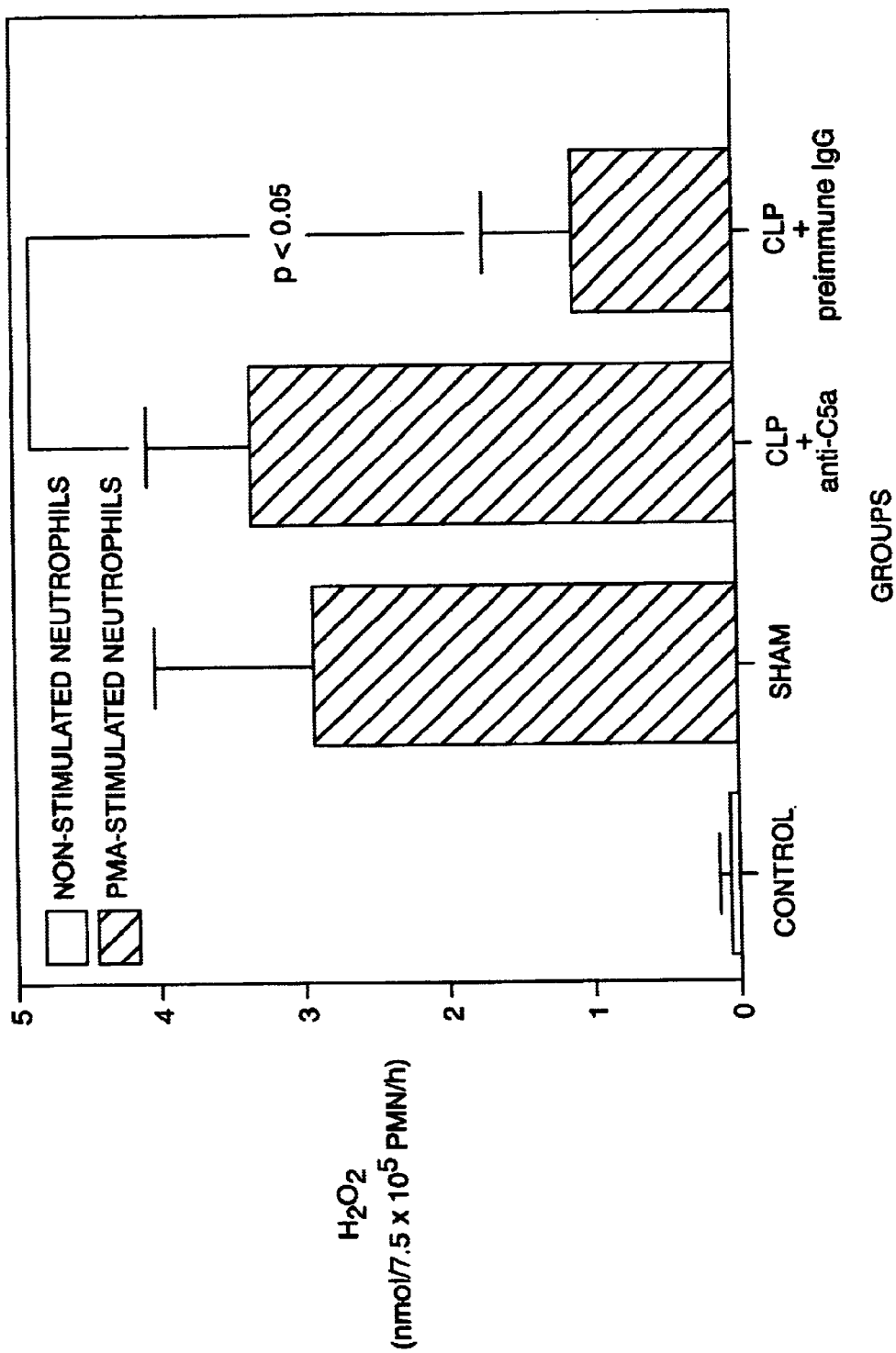
FIG. 4 shows a graph demonstrating the ability of anti-C5a antibodies to increase the level of $H_2O_2$ production in neutrophils of septic rats.

The data collected from this procedure is shown in FIG. 4. Very little $H_2O_2$ (circa 0.1 nmol) was produced in unstimulated blood neutrophils obtained from sham rats or from CLP rats pre-treated with preimmune IgG or anti-C5a IgG. After PMA stimulation, neutrophils from sham rats produced 3.1±0.75 nmol $H_2O_2$. In CLP rats treated with preimmune IgG, $H_2O_2$ production of PMA-stimulated neutrophils was reduced by nearly 62%, to 1.25±0.50 nmol. In striking contrast, blood neutrophils from CLP animals treated with anti-C5a demonstrated full $H_2O_2$ generation, 3.58±0.67 nmol after in vitro stimulation with PMA, indicating that treatment with anti-C5a antibodies preserved this response in neutrophils from CLP rats.

EXAMPLE 7

C5a Peptides Reduce Chemotaxis of Human Neutrophils

This Example describes the ability of certain synthetic peptides representative of regions of human C5a peptide to reduce the chemotactic response of human neutrophils to human C5a peptide. Human neutrophils were isolated from human blood by traditional Ficoll-Hypaque sedimentation techniques. Using standardized methodology, neutrophils ($5 \times 10^6$/ml) labeled with 1 μg/ml BCECF [2', 7'-(2 carboxyethyl)-5-(and-6)-carboxyfluroscein, acetoxymethy ester) at 37° C. for 30 min, were applied to the upper compartments of chemotactic chambers and evaluated for their motility responses to 10 nM human C5a peptide (SEQ ID NO:3) added to the lower compartments. The two compartments were separated by a membrane with pore sizes of 3 μm. Neutrophil chemotactic responses were quantitated by cytofluorometry.

Figure 5:
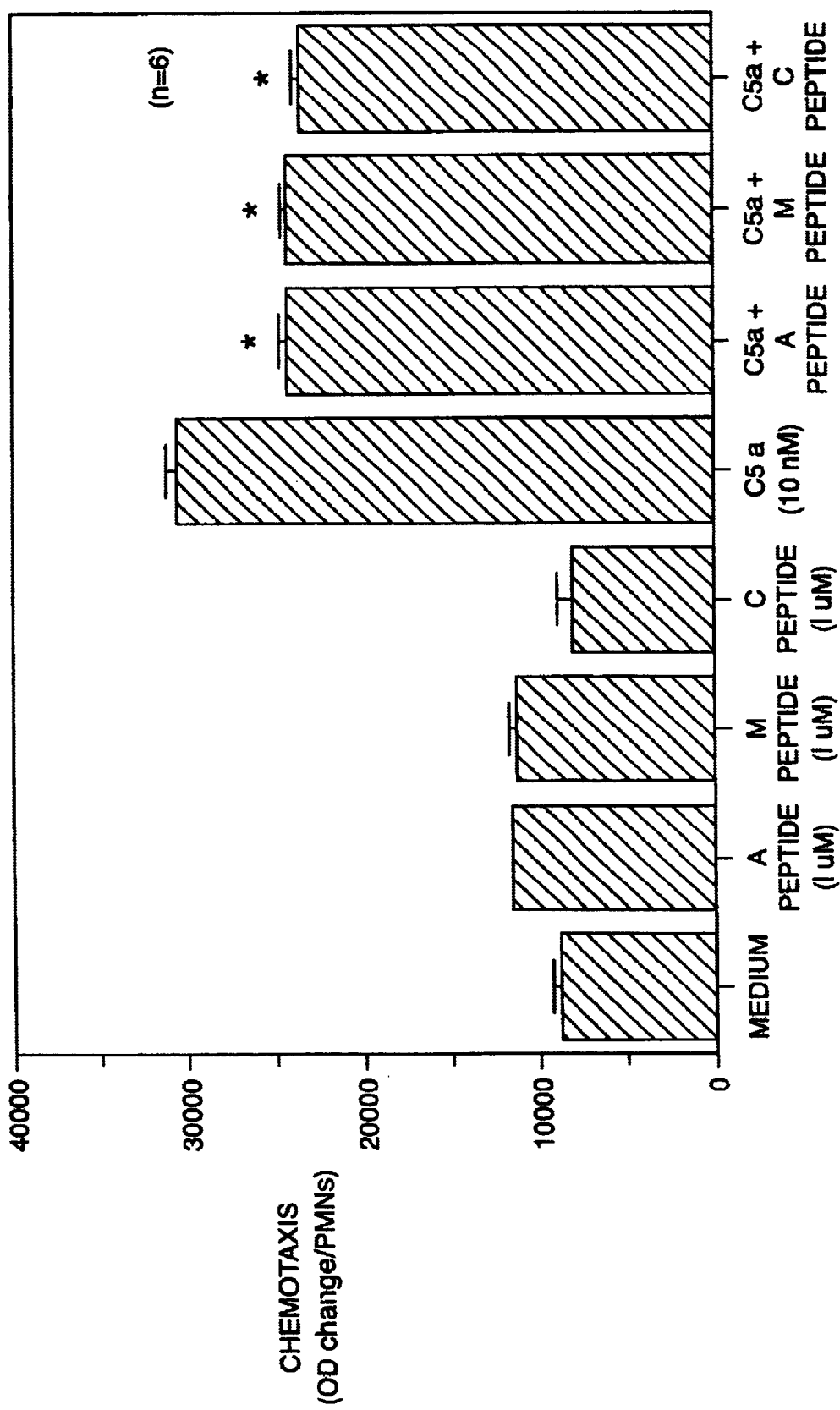
FIG. 5 shows a graph demonstrating the ability of synthetic peptides to reduce human C5a-induced chemotaxis of neutrophils.

Three different peptides, labelled A, M, and C, were also added separately to the lower compartments, at a concentration of 1 μM, in medium alone or together with 10 nM human recombinant C5a peptide. Peptide A (SEQ ID NO:4) represents residues 1–20 of human C5a peptide, peptide M (SEQ ID NO: 5) represents residues 21–40 of human C5a peptide, and peptide C (SEQ ID NO:6) represents residues 55–74 of human C5a peptide. As shown in FIG. 5, the presence of 1 μM from regions A, M, or C, did not per se induce any chemotactic responses. However, the presence of 1 μM of any of these three peptides with 10 μM human C5a resulted in significant reduction (approximately 20%) in the chemotactic responses of neutrophils. This data suggests that peptides from the N-terminal, mid-portion, and C-terminal regions of human C5a have the ability to compete functionally with intact C5a peptide, while demonstrating no intrinsic chemotactic activity.

EXAMPLE 8

Neutrophil Chemotactic Activity of C5a Peptides Linked to KLH

This Example describes neutrophil chemotactic activity of peptides A, M, and C linked to keyholelimpet hemocyanin (KLH) employing the chemotactic assay described in Example 7. The peptide:KLH molar ratios employed were approximately 3:1. The chemotactic responses of neutrophils was evaluated to medium alone, to 10 nM recombinant C5a peptide (SEQ ID NO:3), and to the KLH-A, M, or C conjugates (SEQ ID NOS:4, 5, and 6 respectively), at the calculated synthetic peptide concentrations of 100 nM.

Figure 6:
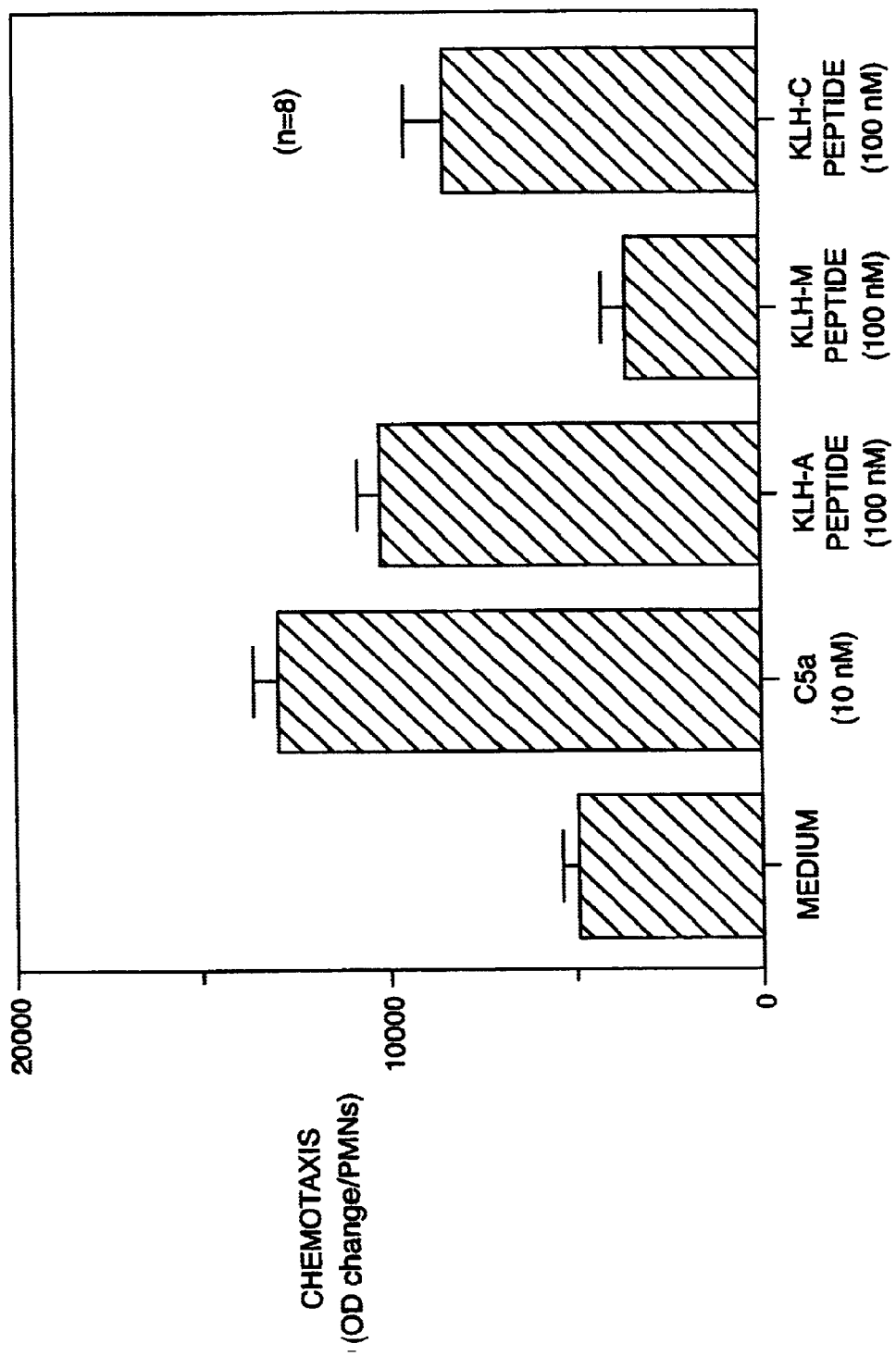
FIG. 6 shows the chemotactic activity of KLH-linked synthetic peptides of human C5a peptide.

The data collected in this Example is shown in FIG. 6. The A peptide KLH conjugate was the most chemotactically active compound when compared to C5a peptide, while the C peptide conjugate was almost as active. The M peptide conjugate revealed no chemotactic activity.

EXAMPLE 9

Polyclonal Rabbit Anti-Human C5a Reactivity with Human C5a Peptide

Figure 7:
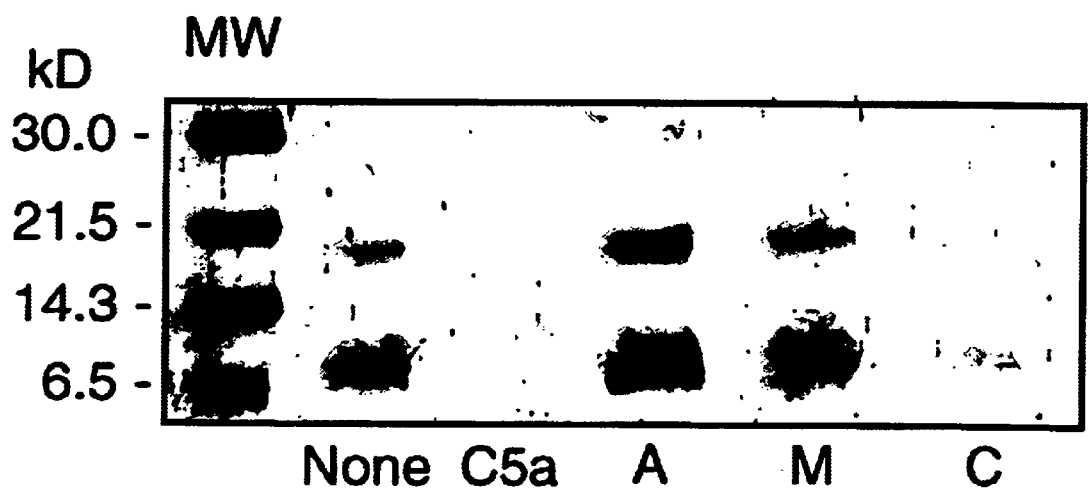
FIG. 7 shows polyclonal rabbit anti-human C5a reactivity with regions of human C5a peptide.

In this Example epitopes in human C5a peptide were evaluated for reactivity with commercially available rabbit polyclonal anti-human C5a antibodies (purchased from Calbiochem-Novabiochem Corp., San Diego, Calif.). Thirty-four (34) μg of this polyclonal anti-human C5a IgG was incubated with 20 μg KLH peptide conjugates (A, M, C, as described in Example 8) for 18 hours at 4° C. Treated and untreated antibodies were then evaluated for their ability to react with recombinant human C5a peptide by Western blot analysis. Fifty (50) ng C5a peptide was added to each lane, and electrophoresis was carried out. As shown in FIG. 7, two banding patterns (one between the 6.5 and 14.3 kDa markers and the other near the 21.4 kDa marker) were found by Western blot analysis. When anti-C5a antibody was incubated with human recombinant C5a peptide, both bands disappeared in Western blots. Preabsorption of the antibody with C peptide abolished the slower band and nearly abolished the faster migrating band. Absorption with M peptide greatly diminished the intensity of both bands, while preabsorption with A peptide showed little evidence of removal of reactivity of the antibody with C5a peptide. This data suggests that the commercially available polyclonal rabbit antibody to human C5a peptide is most reactive with the C terminal region of C5a peptide (represented by peptide C), less reactive with the mid-region of C5a (represented by peptide M), and little, if at all, reactive with the N terminal region of human C5a (represented by peptide A).

EXAMPLE 10

Peptides Which Antagonize the Binding of Human C5a Peptide to Neutrophils

This Examples describes certain peptides which are able to antagonize the ability of human C5a peptide to bind to human neutrophils. Three different peptides, labelled A, M, and C, were used to antagonize the binding of $^{125}$I-hC5a peptide to human neutrophils. Again, peptide A (SEQ ID NO:4) represents residues 1–20 of human C5a peptide, peptide M (SEQ ID NO: 5) represents residues 21–40 of human C5a peptide, and peptide C (SEQ ID NO:6) represents residues 55–74 of human C5a peptide.

Human peripheral blood neutrophils ($1 \times 10^7$ cells/ml) were incubated in Hank's buffered saline plus 0.1% bovine serum albumin with both $^{125}$I-labelled hC5a peptide (300 μCi/nmol) and either peptide A, M, or C, in a final volume of 200 μl in a microfuge tube. The ratio of the shorter peptides (A, M, or C) to $^{125}$I-labelled hC5a peptide was 10:1. After incubation, cell suspension were layered over a 20% sucrose gradient and were sedimented by centrifugation at 11,000 g. The tubes were then frozen on dry ice, followed by cutting the tips containing the pellet. Cell-bound label was then determined by placing the tips in a gamma counter.

Figure 9:
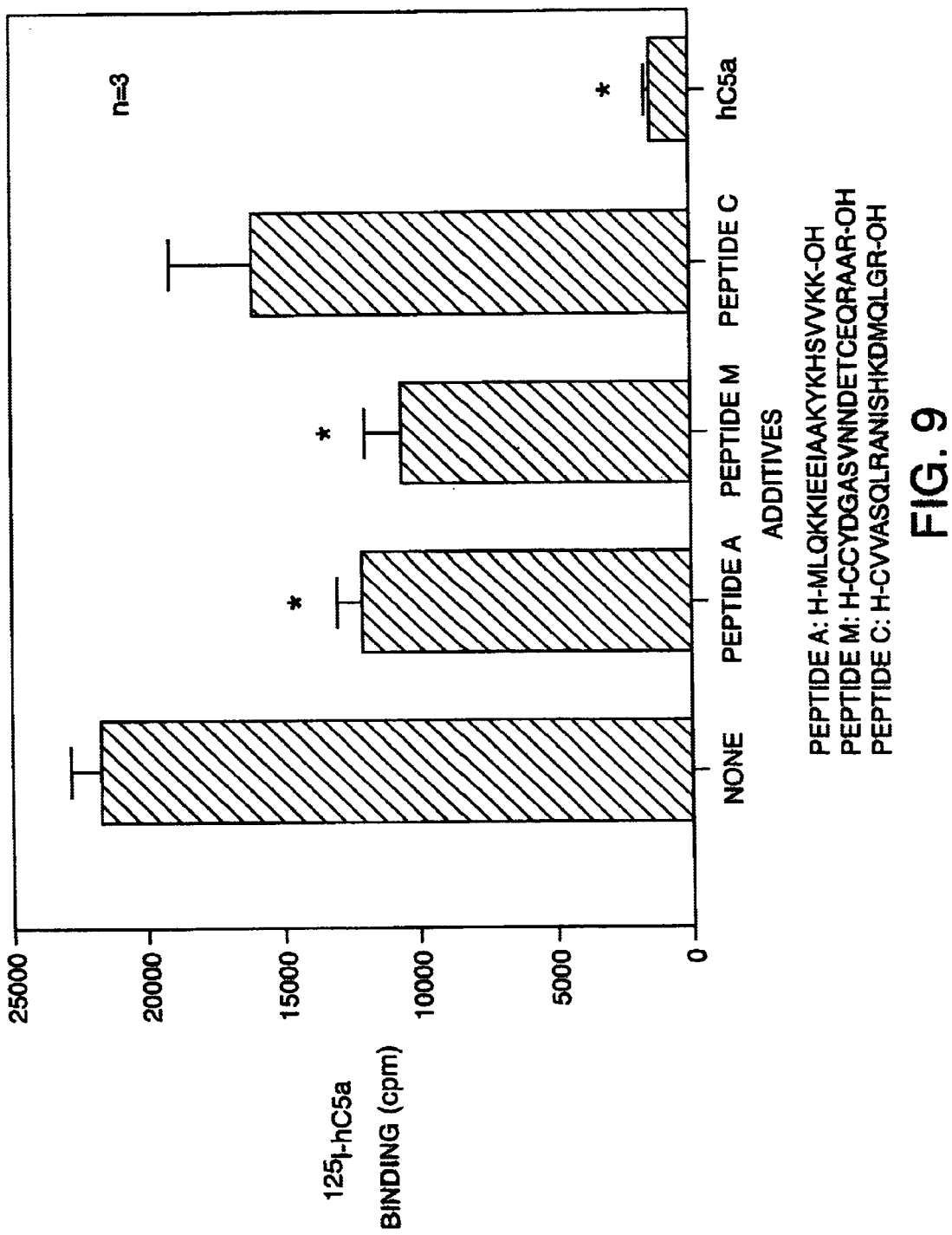
FIG. 9 shows a graph demonstrating the ability of certain synthetic peptides to inhibit the binding of human C5a peptide to human neutrophils.
Figure 10:
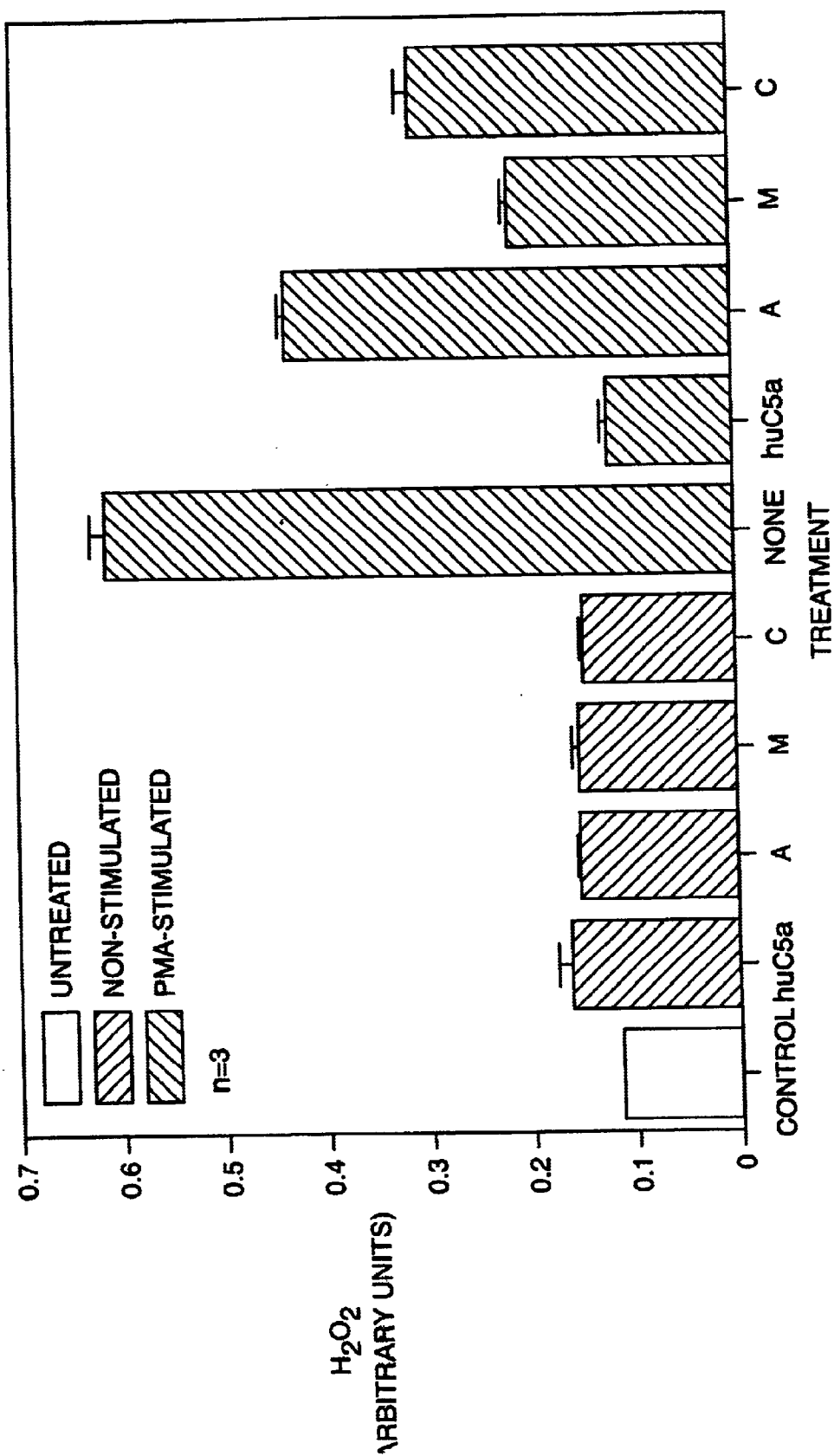
FIG. 10 shows inhibition of the $H_2O_2$ response to PMA by C5a peptide.
Figure 11:
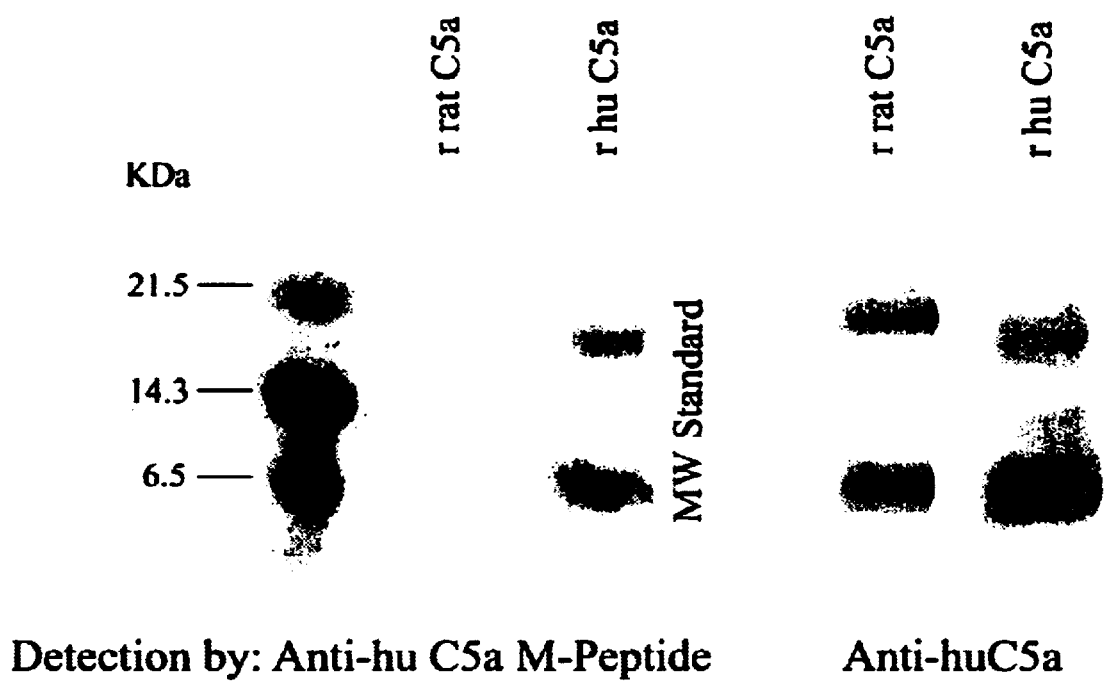
FIG. 11 shows a Western Blot demonstrating specificity of anti-human C5a antibodies for human C5a peptide.

As shown in FIG. 9, peptides A and M were significantly ($p<0.05$) competitive in reducing the binding of hC5a peptide, whereas the C terminal peptide (peptide C) showed no statistically significant interference.

EXAMPLE 11

Screening Candidate Peptides or Useful Immunogens

This Example describes three methods which are employed in screening candidate C-terminal truncated C5a peptides for useful immunogens (i.e. which can be used to produce the anti-C5a antibodies of the present invention). One method involves screening C-terminal truncated C5a peptides which inhibit the chemotaxis of neutrophils. Another method involves screening peptides for the ability to antagonize the binding of C5a peptides to neutrophils. A third method involves administering candidate C-terminal truncated C5a peptides to septic animals and monitoring their response.

The first method, as described in Examples 7 and 8, is used to screen candidate C-terminal truncated C5a peptides which inhibit the chemotaxis of neutrophils. With this method, human neutrophils are isolated from human blood by traditional Ficoll-Hypaque sedimentation techniques.

Using standardized methodology, neutrophils are applied to the upper compartments of chemotactic chambers and evaluated for their motility responses to 10 nM human C5a peptide (SEQ ID NO:3) added to the lower compartments. The two compartments are separated by a membrane with pore sizes of 3 µm. Neutrophil chemotactic responses are quantitated by cytofluorometry.

A candidate C-terminal truncated peptide (1 µM), which may be linked to KLH, is added to the lower compartments in medium alone or together with 10 nM human recombinant C5a peptide. The chemotactic response of the neutrophils is then quantitated by cytofluorometry. One indication of a useful immunogen is if the candidate C-terminal truncated C5a peptide induces chemotaxis of the neutrophils as compared to human C5a peptide alone. Another indication of a useful immunogen is if the candidate C-terminal truncated C5a peptide inhibits chemotaxis of neutrophils when combined with human C5a peptide, as compared to human C5a peptide alone.

A second method, as described in Example 10, is used to screen candidate C-terminal truncated C5a peptides which antagonize the binding of $^{125}$I-C5a peptide to neutrophils. In this Example, human neutrophils are incubated with human $^{125}$I-C5a peptide and the candidate C-terminal truncated C5a peptide. Inhibition of $^{125}$I-C5a peptide binding to the neutrophils by the candidate C-terminal truncated peptide indicates a potentially useful immunogen for the production of anti-C5a antibodies.

A third method employs the septic rats described in Example 1. In this Example, one group of CLP sepsis induced rats is administered 50 mg/kg of a candidate C-terminal C5a truncated peptide intravenously immediately after the CLP procedure, while a second group of CLP rats is used as a control. Survival rates and symptoms of sepsis are recorded over a ten day period. Candidate C-terminal truncated C5a peptides which reduce the symptoms of sepsis, and/or increase survival times as compared to the control group are considered potential immunogens for producing anti-C5a antibodies.

EXAMPLE 12

$H_2O_2$ Production of Human Neutrophils in the Presence of Short C5a Peptides This Example describes the effect of human C5a peptide, and certain shorter synthetic human C5a peptides A, M, or C, to inhibit the $H_2O_2$ production of human neutrophils stimulated by phorbol myristate acetate (PMA). Again, peptide A (SEQ ID NO:4) represents residues 1–20 of human C5a peptide, peptide M (SEQ ID NO: 5) represents residues 2 1–40 of human C5a peptide, and peptide C (SEQ ID NO:6) represents residues 55–74 of human C5a peptide. Human neutrophils were isolated and then pretreated with C5a peptide or one of the shorter synthetic peptides (A, M, or C). Cells were then stimulated with PMA and the production of $H_2O_2$ was measured.

As shown in FIG. 10, C5a peptide and the shorter peptides alone have no effect on $H_2O_2$ production. However, PMA elicits a strong $H_2O_2$ response, which is inhibitable by the C5a peptide, and to varying degrees by peptides A, M, and C. Peptide M was shown to exert the strongest suppression of $H_2O_2$ production of all of the peptides (See FIG. 10).

EXAMPLE 13

Preparation and Characterization of Anti-Human C5a Antibodies

This Example describes the production of anti-human C5a antibodies. A short human C5a peptide with the sequence CCYDGASVNNDETCEQRAAR (peptide M, SEQ ID NO:5) was obtained from Research Genetics (Huntsville Ala.) and coupled to keyhole limpet hemocyanin (KLH). The coupled peptide was used as an antigen to immunize rabbits. After several injections, the antibody was recovered by affinity purification.

A Western Blot was then used to demonstrate that these anti-human C5a antibodies are specific for human C5a peptide, and not rat C5a peptide. Briefly, recombinant human and rat C5a peptide were run in parallel on a gel, and transferred to a filter. The filter was blocked, and then probed with the anti-human C5a antibody. The resulting signal revealed that the anti-human C5a antibody was only able to recognize human C5a peptide, and not rat C5a peptide (See FIG. 11).

An additional Western blot was also performed in order to determine if polyclonal anit-human antibodies (commercially available from Calbiochem) shared this type of specificity. Again, recombinant human and rat C5a peptide were run in parallel on a gel, and transferred to a filter. The filter was blocked, and then probed with the commercially available polyclonal anti-C5a antibody. The resulting signal revealed that the polyclonal anti-human C5a antibody was able to recognize both human and rat C5a peptide (See FIG. 11). As such, it is clear that the commercially available polyclonal anti-human C5a antibody does not have the same type of specificity as the anti-human C5a antibody discussed above.

EXAMPLE 14

Therapeutic use of Anti-Human C5a Antibodies to Treat Sepsis in Humans

Anti-C5a antibodies may be used prophylactically or therapeutically to treat sepsis in humans. Individuals at risk of contracting sepsis, particularly patients undergoing surgery, or those with sepsis may be administered an effective amount of anti-C5a antibodies to prevent or reduce the severity of the disease. A typical treatment regimen would consist of administering 5–10 mg of antibody per kilogram of patient body weight. Prophylactically the dose would be given just prior to surgery, and repeated at least once immediately thereafter. Therapeutically the dose would be given every 24–48 hours until remission of the disease is apparent. The initial therapeutic dose would be 25 mg per kilogram of patient body weight, and then reduced to 5–10 mg per kilogram. The antibody may be administered by any number of routes, but the preferred route of administration is intravenously.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in biochemistry, immunology, chemistry, molecular biology, the medical profession or related fields are intended to be within the scope of the following claims.

SEQUENCE LISTING

<160> NUMBER OF SEQ ID NOS: 74

<210> SEQ ID NO 1
<211> LENGTH: 77
<212> TYPE: PRT
<213> ORGANISM: Rattus norvegicus

<400> SEQUENCE: 1

Asp Leu Gln Leu Leu His Gln Lys Val Glu Glu Ala Ala Lys Tyr
 1               5                  10                  15

Lys His Arg Val Pro Lys Lys Cys Cys Tyr Asp Gly Ala Arg Glu Asn
                20                  25                  30

Lys Tyr Glu Thr Cys Glu Gln Arg Val Ala Arg Val Thr Ile Gly Pro
            35                  40                  45

His Cys Ile Arg Ala Phe Asn Glu Cys Cys Thr Ile Ala Asp Lys Ile
        50                  55                  60

Arg Lys Glu Ser His His Lys Gly Met Leu Leu Gly Arg
65                  70                  75

<210> SEQ ID NO 2
<211> LENGTH: 20
<212> TYPE: PRT
<213> ORGANISM: Rattus norvegicus

<400> SEQUENCE: 2

Lys His Arg Val Pro Lys Lys Cys Cys Tyr Asp Gly Ala Arg Glu Asn
 1               5                  10                  15

Lys Tyr Glu Thr
            20

<210> SEQ ID NO 3
<211> LENGTH: 74
<212> TYPE: PRT
<213> ORGANISM: Homo sapiens

<400> SEQUENCE: 3

Met Leu Gln Lys Lys Ile Glu Glu Ile Ala Ala Lys Tyr Lys His Ser
 1               5                  10                  15

Val Val Lys Lys Cys Cys Tyr Asp Gly Ala Ser Val Asn Asn Asp Glu
                20                  25                  30

Thr Cys Glu Gln Arg Ala Ala Arg Ile Ser Leu Gly Pro Arg Cys Ile
            35                  40                  45

Lys Ala Phe Thr Glu Cys Cys Val Val Ala Ser Gln Leu Arg Ala Asn
        50                  55                  60

Ile Ser His Lys Asp Met Gln Leu Gly Arg
65                  70

<210> SEQ ID NO 4
<211> LENGTH: 20
<212> TYPE: PRT
<213> ORGANISM: Homo sapiens

<400> SEQUENCE: 4

Met Leu Gln Lys Lys Ile Glu Glu Ile Ala Ala Lys Tyr Lys His Ser
 1               5                  10                  15

Val Val Lys Lys
            20

```
<210> SEQ ID NO 5
<211> LENGTH: 20
<212> TYPE: PRT
<213> ORGANISM: Homo sapiens

<400> SEQUENCE: 5

Cys Cys Tyr Asp Gly Ala Ser Val Asn Asn Asp Glu Thr Cys Glu Gln
 1               5                  10                  15

Arg Ala Ala Arg
            20

<210> SEQ ID NO 6
<211> LENGTH: 20
<212> TYPE: PRT
<213> ORGANISM: Homo sapiens

<400> SEQUENCE: 6

Cys Val Val Ala Ser Gln Leu Arg Ala Asn Ile Ser His Lys Asp Met
 1               5                  10                  15

Gln Leu Gly Arg
            20

<210> SEQ ID NO 7
<211> LENGTH: 74
<212> TYPE: PRT
<213> ORGANISM: Bos taurus

<400> SEQUENCE: 7

Met Leu Lys Lys Lys Ile Glu Glu Ala Ala Lys Tyr Arg Asn Ala
 1               5                  10                  15

Trp Val Lys Cys Cys Tyr Asp Gly Ala His Arg Asn Asp Asp Glu
            20                  25                  30

Thr Cys Glu Glu Arg Ala Ala Arg Ile Ala Ile Gly Pro Glu Cys Ile
        35                  40                  45

Lys Ala Phe Lys Ser Cys Cys Ala Ile Ala Ser Gln Phe Arg Ala Asp
     50                  55                  60

Glu His His Lys Asn Met Gln Leu Gly Arg
 65                  70

<210> SEQ ID NO 8
<211> LENGTH: 74
<212> TYPE: PRT
<213> ORGANISM: Sus scrofa

<400> SEQUENCE: 8

Met Leu Gln Lys Lys Ile Glu Glu Ala Ala Lys Tyr Lys Tyr Ala
 1               5                  10                  15

Met Leu Lys Lys Cys Cys Tyr Asp Gly Ala Tyr Arg Asn Asp Asp Glu
            20                  25                  30

Thr Cys Glu Glu Arg Ala Ala Arg Ile Lys Ile Gly Pro Lys Cys Val
        35                  40                  45

Lys Ala Phe Lys Asp Cys Cys Tyr Ile Ala Asn Gln Val Arg Ala Glu
     50                  55                  60

Gln Ser His Lys Asn Ile Gln Leu Gly Arg
 65                  70

<210> SEQ ID NO 9
<211> LENGTH: 242
<212> TYPE: DNA
<213> ORGANISM: Homo sapiens
```

-continued

```
<400> SEQUENCE: 9
gatccagtat gttgcaaaaa aaaattgaag aaattgctgc taaatataaa cattctgttg      60
ttaaaaaatg ttgttatgat ggagcttctg ttaataatga tgaaacctgc gaacaacgcg     120
ctgctagaat ttctttggga cctagatgta ttaaagcatt tacagaatgt tgtgttgttg     180
cttctcaatt gaggcgaata tttctcataa agatatgcaa ttgggaagat aggatccgtc     240
ga                                                                    242

<210> SEQ ID NO 10
<211> LENGTH: 60
<212> TYPE: DNA
<213> ORGANISM: Homo sapiens

<400> SEQUENCE: 10
atgttgcaaa aaaaattga agaaattgct gctaaatata acattctgt tgttaaaaaa       60

<210> SEQ ID NO 11
<211> LENGTH: 60
<212> TYPE: DNA
<213> ORGANISM: Homo sapiens

<400> SEQUENCE: 11
tgttgttatg atggagcttc tgttaataat gatgaaacct gcgaacaacg cgctgctaga     60

<210> SEQ ID NO 12
<211> LENGTH: 231
<212> TYPE: DNA
<213> ORGANISM: Rattus norvegicus

<400> SEQUENCE: 12
gacctgcagc tcctgcatca gaaagtggaa gaacaagctg ctaaatacaa acaccgtgtg      60
cccaagaaat gctgttatga tggagcccga gaaaacaaat acgaaacctg tgagcagcga    120
gttgcccggg tgaccatagg cccacactgc atcagggcct caacgagtg ttgtactatt     180 gcggataaga tccgaaaaga aagccaccac aaaggcatgc tgttgggaag g             231

<210> SEQ ID NO 13
<211> LENGTH: 60
<212> TYPE: DNA
<213> ORGANISM: Rattus norvegicus

<400> SEQUENCE: 13
aaacaccgtg tgcccaagaa atgctgttat gatggagccc gagaaaacaa atacgaaacc     60

<210> SEQ ID NO 14
<211> LENGTH: 9
<212> TYPE: PRT
<213> ORGANISM: Homo sapiens

<400> SEQUENCE: 14

Lys Tyr Lys His Ser Val Val Lys Lys
 1               5

<210> SEQ ID NO 15
<211> LENGTH: 6
<212> TYPE: PRT
<213> ORGANISM: Homo sapiens

<400> SEQUENCE: 15

Val Asn Asn Asp Glu Thr
 1               5
```

```
<210> SEQ ID NO 16
<211> LENGTH: 9
<212> TYPE: PRT
<213> ORGANISM: Homo sapiens

<400> SEQUENCE: 16

Ala Ala Arg Ile Ser Leu Gly Pro Arg
 1               5

<210> SEQ ID NO 17
<211> LENGTH: 27
<212> TYPE: DNA
<213> ORGANISM: Homo sapiens

<400> SEQUENCE: 17
ttgctgctaa atataaacat tctgttg                                       27

<210> SEQ ID NO 18
<211> LENGTH: 18
<212> TYPE: DNA
<213> ORGANISM: Homo sapiens

<400> SEQUENCE: 18
gagcttctgt taataatg                                                 18

<210> SEQ ID NO 19
<211> LENGTH: 27
<212> TYPE: DNA
<213> ORGANISM: Homo sapiens

<400> SEQUENCE: 19
aacaacgcgc tgctagaatt tctttgg                                       27

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 20

Lys Tyr Lys His Thr Val Val Lys Lys
 1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 21

Lys Tyr Lys His Ser Ala Val Lys Lys
 1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 22

Lys Tyr Lys His Ser Ala Ala Lys Lys
```

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 23

Lys Tyr Lys His Ser Val Ala Lys Lys
 1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic

<400> SEQUENCE: 24

Val Asn Asn Gln Glu Thr
 1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic

<400> SEQUENCE: 25

Val Asn Asn Asp Glu Ser
 1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic

<400> SEQUENCE: 26

Val Asn Asn Gln Glu Ser
 1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic

<400> SEQUENCE: 27

Ala Asn Asn Asp Glu Thr
 1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 28

Ala Ala Arg Ile Ser Ile Gly Pro Arg
 1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 29

Ala Ala Arg Ile Ser Val Gly Pro Arg
 1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 30

Ala Ala Arg Ile Thr Leu Gly Pro Arg
 1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 31

Ala Val Arg Ile Ser Leu Gly Pro Arg
 1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 32

Val Ala Arg Ile Ser Leu Gly Pro Arg
 1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 33

Val Val Arg Ile Ser Leu Gly Pro Arg
 1               5

<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence: Synthetic

<400> SEQUENCE: 34

Met Leu Gln Lys Lys Ile Glu Glu Ile Ala Ala Lys Tyr Lys His Ser
 1               5                  10                  15

Val Val Lys

<210> SEQ ID NO 35
<211> LENGTH: 18
<212> TYPE: PRT
<213> ORGANISM: Artificial Sequence
<220> FEATURE:
<223> OTHER INFORMATION: Description of Artificial Sequence: Synthetic

<400> SEQUENCE: 35

Met Leu Gln Lys Lys Ile Glu Glu Ile Ala Ala Lys Tyr Lys His Ser
 1               5                  10                  15

Val Val

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic

<400> SEQUENCE: 36

Met Leu Gln Lys Lys Ile Glu Glu Ile Ala Ala Lys Tyr Lys His Ser
 1               5                  10                  15

Val

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: Synthetic

<400> SEQUENCE: 37

Met Leu Gln Lys Lys Ile Glu Glu Ile Ala Ala Lys Tyr Lys His Ser
 1               5                  10                  15

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 38

Met Leu Gln Lys Lys Ile Glu Glu Ile Ala Ala Lys Tyr Lys His
 1               5                  10                  15

<210> SEQ ID NO 39
<211> LENGTH: 19
<212> TYPE: PRT
<213> ORGANISM: Artificial Sequence
<220> FEATURE:
<223> OTHER INFORMATION: Description of Artificial Sequence: Synthetic

<400> SEQUENCE: 39

Leu Gln Lys Lys Ile Glu Glu Ile Ala Ala Lys Tyr Lys His Ser Val
 1               5                  10                  15

Val Lys Lys

<210> SEQ ID NO 40
<211> LENGTH: 18
<212> TYPE: PRT
<213> ORGANISM: Artificial Sequence
<220> FEATURE:

<223> OTHER INFORMATION: Description of Artificial Sequence: Synthetic

<400> SEQUENCE: 40

Gln Lys Lys Ile Glu Glu Ile Ala Ala Lys Tyr Lys His Ser Val Val
 1               5                  10                  15
Lys Lys

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic

<400> SEQUENCE: 41

Lys Lys Ile Glu Glu Ile Ala Ala Lys Tyr Lys His Ser Val Val Lys
 1               5                  10                  15
Lys

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic

<400> SEQUENCE: 42

Lys Ile Glu Glu Ile Ala Ala Lys Tyr Lys His Ser Val Val Lys Lys
 1               5                  10                  15

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 43

Ile Glu Glu Ile Ala Ala Lys Tyr Lys His Ser Val Val Lys Lys
 1               5                  10                  15

<210> SEQ ID NO 44
<211> LENGTH: 20
<212> TYPE: PRT
<213> ORGANISM: Artificial Sequence
<220> FEATURE:
<223> OTHER INFORMATION: Description of Artificial Sequence: Synthetic

<400> SEQUENCE: 44

Met Ile Gln Lys Lys Ile Glu Glu Ile Ala Ala Lys Tyr Lys His Ser
 1               5                  10                  15
Val Val Lys Lys
            20

<210> SEQ ID NO 45
<211> LENGTH: 20
<212> TYPE: PRT
<213> ORGANISM: Artificial Sequence
<220> FEATURE:
<223> OTHER INFORMATION: Description of Artificial Sequence: Synthetic

<400> SEQUENCE: 45

Met Val Gln Lys Lys Ile Glu Glu Ile Ala Ala Lys Tyr Lys His Ser
 1               5                  10                  15

Val Val Lys Lys
            20

<210> SEQ ID NO 46
<211> LENGTH: 20
<212> TYPE: PRT
<213> ORGANISM: Artificial Sequence
<220> FEATURE:
<223> OTHER INFORMATION: Description of Artificial Sequence: Synthetic

<400> SEQUENCE: 46

Met Leu Asp Lys Lys Ile Glu Glu Ile Ala Ala Lys Tyr Lys His Ser
  1               5                  10                  15

Val Val Lys Lys
            20

<210> SEQ ID NO 47
<211> LENGTH: 20
<212> TYPE: PRT
<213> ORGANISM: Artificial Sequence
<220> FEATURE:
<223> OTHER INFORMATION: Description of Artificial Sequence: Synthetic

<400> SEQUENCE: 47

Met Leu Gln Lys Lys Ile Glu Glu Ile Ala Ala Lys Tyr Lys His Thr
  1               5                  10                  15

Val Val Lys Lys
            20

<210> SEQ ID NO 48
<211> LENGTH: 20
<212> TYPE: PRT
<213> ORGANISM: Artificial Sequence
<220> FEATURE:
<223> OTHER INFORMATION: Description of Artificial Sequence: Synthetic

<400> SEQUENCE: 48

Met Leu Gln Lys Lys Ile Glu Glu Ile Val Ala Lys Tyr Lys His Ser
  1               5                  10                  15

Val Val Lys Lys
            20

<210> SEQ ID NO 49
<211> LENGTH: 20
<212> TYPE: PRT
<213> ORGANISM: Artificial Sequence
<220> FEATURE:
<223> OTHER INFORMATION: Description of Artificial Sequence: Synthetic

<400> SEQUENCE: 49

Met Leu Gln Lys Lys Ile Glu Glu Ile Val Val Lys Tyr Lys His Ser
  1               5                  10                  15

Val Val Lys Lys
            20

<210> SEQ ID NO 50
<211> LENGTH: 20
<212> TYPE: PRT
<213> ORGANISM: Artificial Sequence
<220> FEATURE:
<223> OTHER INFORMATION: Description of Artificial Sequence: Synthetic

<400> SEQUENCE: 50

Met Leu Gln Lys Lys Ile Glu Glu Ile Ala Ala Lys Tyr Lys His Ser
  1               5                  10                  15

Val Ala Lys Lys
            20

<210> SEQ ID NO 51
<211> LENGTH: 20
<212> TYPE: PRT
<213> ORGANISM: Artificial Sequence
<220> FEATURE:
<223> OTHER INFORMATION: Description of Artificial Sequence: Synthetic

<400> SEQUENCE: 51

Met Leu Gln Lys Lys Ile Glu Glu Ile Ala Ala Lys Tyr Lys His Ser
 1               5                  10                  15

Ala Ala Lys Lys
            20

<210> SEQ ID NO 52
<211> LENGTH: 20
<212> TYPE: PRT
<213> ORGANISM: Artificial Sequence
<220> FEATURE:
<223> OTHER INFORMATION: Description of Artificial Sequence: Synthetic

<400> SEQUENCE: 52

Met Leu Gln Lys Lys Ile Glu Glu Ile Ala Ala Lys Tyr Lys His Ser
 1               5                  10                  15

Ala Val Lys Lys
            20

<210> SEQ ID NO 53
<211> LENGTH: 20
<212> TYPE: PRT
<213> ORGANISM: Artificial Sequence
<220> FEATURE:
<223> OTHER INFORMATION: Description of Artificial Sequence: Synthetic

<400> SEQUENCE: 53

Met Leu Gln Lys Lys Ile Glu Glu Ile Ala Val Lys Tyr Lys His Ser
 1               5                  10                  15

Val Val Lys Lys
            20

<210> SEQ ID NO 54
<211> LENGTH: 19
<212> TYPE: PRT
<213> ORGANISM: Artificial Sequence
<220> FEATURE:
<223> OTHER INFORMATION: Description of Artificial Sequence: Synthetic

<400> SEQUENCE: 54

Cys Cys Tyr Asp Gly Ala Ser Val Asn Asn Asp Glu Thr Cys Glu Gln
 1               5                  10                  15

Arg Ala Ala

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic

<400> SEQUENCE: 55

Cys Cys Tyr Asp Gly Ala Ser Val Asn Asn Asp Glu Thr Cys Glu Gln
 1               5                  10                  15

Arg Ala

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic

<400> SEQUENCE: 56

Cys Cys Tyr Asp Gly Ala Ser Val Asn Asn Asp Glu Thr Cys Glu Gln
 1               5                  10                  15

Arg

<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence: Synthetic

<400> SEQUENCE: 57

Cys Cys Tyr Asp Gly Ala Ser Val Asn Asn Asp Glu Thr Cys Glu Gln
 1               5                  10                  15

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 58

Cys Cys Tyr Asp Gly Ala Ser Val Asn Asn Asp Glu Thr Cys Glu
 1               5                  10                  15

<210> SEQ ID NO 59
<211> LENGTH: 19
<212> TYPE: PRT
<213> ORGANISM: Artificial Sequence
<220> FEATURE:
<223> OTHER INFORMATION: Description of Artificial Sequence: Synthetic

<400> SEQUENCE: 59

Cys Tyr Asp Gly Ala Ser Val Asn Asn Asp Glu Thr Cys Glu Gln Arg
 1               5                  10                  15

Ala Ala Arg

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic

<400> SEQUENCE: 60

Tyr Asp Gly Ala Ser Val Asn Asn Asp Glu Thr Cys Glu Gln Arg Ala
 1               5                  10                  15

Ala Arg

<210> SEQ ID NO 61
<211> LENGTH: 17
<212> TYPE: PRT
<213> ORGANISM: Artificial Sequence

```
<220> FEATURE:
<223> OTHER INFORMATION: Description of Artificial Sequence: Synthetic

<400> SEQUENCE: 61

Asp Gly Ala Ser Val Asn Asn Asp Glu Thr Cys Glu Gln Arg Ala Ala
 1               5                  10                  15

Arg

<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence: Synthetic

<400> SEQUENCE: 62

Gly Ala Ser Val Asn Asn Asp Glu Thr Cys Glu Gln Arg Ala Ala Arg
 1               5                  10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 63

Ala Ser Val Asn Asn Asp Glu Thr Cys Glu Gln Arg Ala Ala Arg
 1               5                  10                  15

<210> SEQ ID NO 64
<211> LENGTH: 20
<212> TYPE: PRT
<213> ORGANISM: Artificial Sequence
<220> FEATURE:
<223> OTHER INFORMATION: Description of Artificial Sequence: Synthetic

<400> SEQUENCE: 64

Cys Cys Tyr Gln Gly Ala Ser Val Asn Asn Asp Glu Thr Cys Glu Gln
 1               5                  10                  15

Arg Ala Ala Arg
            20

<210> SEQ ID NO 65
<211> LENGTH: 20
<212> TYPE: PRT
<213> ORGANISM: Artificial Sequence
<220> FEATURE:
<223> OTHER INFORMATION: Description of Artificial Sequence: Synthetic

<400> SEQUENCE: 65

Cys Cys Tyr Asp Gly Ala Ser Val Asn Asn Gln Glu Thr Cys Glu Gln
 1               5                  10                  15

Arg Ala Ala Arg
            20

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic

<400> SEQUENCE: 66

Cys Cys Tyr Gln Gly Ala Ser Val Asn Asn Gln Glu Thr Cys Glu Gln
```

```
                 1               5              10              15

Arg Ala Ala Arg
            20

<210> SEQ ID NO 67
<211> LENGTH: 20
<212> TYPE: PRT
<213> ORGANISM: Artificial Sequence
<220> FEATURE:
<223> OTHER INFORMATION: Description of Artificial Sequence:  Synthetic

<400> SEQUENCE: 67

Cys Cys Tyr Asp Gly Ala Ser Val Asn Asn Asp Glu Ser Cys Glu Gln
  1               5              10              15

Arg Ala Ala Arg
            20

<210> SEQ ID NO 68
<211> LENGTH: 20
<212> TYPE: PRT
<213> ORGANISM: Artificial Sequence
<220> FEATURE:
<223> OTHER INFORMATION: Description of Artificial Sequence:  Synthetic

<400> SEQUENCE: 68

Cys Cys Tyr Asp Gly Ala Thr Val Asn Asn Asp Glu Thr Cys Glu Gln
  1               5              10              15

Arg Ala Ala Arg
            20

<210> SEQ ID NO 69
<211> LENGTH: 20
<212> TYPE: PRT
<213> ORGANISM: Artificial Sequence
<220> FEATURE:
<223> OTHER INFORMATION: Description of Artificial Sequence:  Synthetic

<400> SEQUENCE: 69

Cys Cys Tyr Asp Gly Val Ser Val Asn Asn Asp Glu Thr Cys Glu Gln
  1               5              10              15

Arg Ala Ala Arg
            20

<210> SEQ ID NO 70
<211> LENGTH: 20
<212> TYPE: PRT
<213> ORGANISM: Artificial Sequence
<220> FEATURE:
<223> OTHER INFORMATION: Description of Artificial Sequence:  Synthetic

<400> SEQUENCE: 70

Cys Cys Tyr Asp Gly Ala Ser Ala Asn Asn Asp Glu Thr Cys Glu Gln
  1               5              10              15

Arg Ala Ala Arg
            20

<210> SEQ ID NO 71
<211> LENGTH: 20
<212> TYPE: PRT
<213> ORGANISM: Artificial Sequence
<220> FEATURE:
<223> OTHER INFORMATION: Description of Artificial Sequence:  Synthetic

<400> SEQUENCE: 71
```

-continued

```
Cys Cys Tyr Asp Gly Ala Ser Val Asn Asn Asp Glu Thr Cys Glu Gln
  1               5                  10                  15

Arg Val Ala Arg
            20

<210> SEQ ID NO 72
<211> LENGTH: 20
<212> TYPE: PRT
<213> ORGANISM: Artificial Sequence
<220> FEATURE:
<223> OTHER INFORMATION: Description of Artificial Sequence: Synthetic

<400> SEQUENCE: 72

Cys Cys Tyr Asp Gly Ala Ser Val Asn Asn Asp Glu Thr Cys Glu Gln
  1               5                  10                  15

Arg Val Val Arg
            20

<210> SEQ ID NO 73
<211> LENGTH: 20
<212> TYPE: PRT
<213> ORGANISM: Artificial Sequence
<220> FEATURE:
<223> OTHER INFORMATION: Description of Artificial Sequence: Synthetic

<400> SEQUENCE: 73

Cys Cys Tyr Asp Gly Ala Ser Val Asn Asn Asp Glu Thr Cys Glu Gln
  1               5                  10                  15

Arg Ala Val Arg
            20

<210> SEQ ID NO 74
<211> LENGTH: 20
<212> TYPE: PRT
<213> ORGANISM: Artificial Sequence
<220> FEATURE:
<223> OTHER INFORMATION: Description of Artificial Sequence: Synthetic

<400> SEQUENCE: 74

Cys Cys Tyr Asp Gly Val Ser Ala Asn Asn Asp Glu Thr Cys Glu Gln
  1               5                  10                  15

Arg Val Val Arg
            20
```

We claim:

1. A method of producing polyclonal antibodies, comprising:
   a) providing;
      i) an animal, and
      ii) an immunogenic composition, wherein said composition comprises a C-terminal truncated C5a peptide selected from the group consisting of SEQ ID NO:2, SEQ ID NO:4, SEQ ID NO:5, SEQ ID NO:14, SEQ ID NO:15, and SEQ ID NO:16; and
   b) immunizing said animal with said immunogenic composition under conditions such that antibodies are generated.

2. The method of claim 1, further comprising step c) recovering said antibodies from said animal.

3. The method of claim 1, wherein said animal is selected from the group consisting of rabbit, mouse, rat, bird, and horse.

* * * * *